(12) United States Patent
Au et al.

(10) Patent No.: US 8,043,631 B2
(45) Date of Patent: Oct. 25, 2011

(54) TUMOR TARGETING DRUG-LOADED PARTICLES

(76) Inventors: Jessie L. S. Au, Columbus, OH (US); M. Guillaume Wientjes, Columbus, OH (US)

(*) Notice: Subject to any disclaimer, the term of this patent is extended or adjusted under 35 U.S.C. 154(b) by 107 days.

(21) Appl. No.: 11/242,546

(22) Filed: Oct. 3, 2005

(65) Prior Publication Data

US 2006/0034925 A1 Feb. 16, 2006

(51) Int. Cl.
*A61K 9/22* (2006.01)
*A61K 31/70* (2006.01)
*A61K 31/355* (2006.01)

(52) U.S. Cl. .......... 424/468; 424/457; 514/34; 514/449; 514/456

(58) Field of Classification Search .................. 424/468, 424/457; 514/34, 449, 456
See application file for complete search history.

(56) References Cited

U.S. PATENT DOCUMENTS

| | | | |
|---|---|---|---|
| 5,702,717 A | 12/1997 | Cha et al. | |
| 6,287,285 B1 * | 9/2001 | Michal et al. | 604/264 |
| 6,506,405 B1 * | 1/2003 | Desai et al. | 424/450 |
| 6,881,420 B2 | 4/2005 | Flashner-Barak et al. | |
| 2004/0247624 A1 * | 12/2004 | Unger et al. | 424/400 |

FOREIGN PATENT DOCUMENTS

WO WO 0061141 * 10/2000

OTHER PUBLICATIONS

Signore et al. J. Vasc. Interv. Radiol. 200112:79-87.*
Alakhov et al, Exp. Opin. Biol. Ther. 2001 1(4):583:602.*
Jessie et al. Cancer research 58 2141-2148 1998.*
www.mesotheliomaweb.org/categories.htm 5 pages 199867.*
J. of Controlled release V 86 (2003) 33-48 is of interest.*
New drugs of 1999 Medscape Today, 1999, 1-14.*
Jae-Woon Korean J. Chem. Eng 17 (2000): 230-236.*
Fonseca et al. (J. Controlled Release 83 (2002) 273-286).*
Mu et al. (J. Controlled Release 86 (2003) 33-48).*
Falcone, A, Pfanner, E. Brunetti, I, et al., Suramin in Combination with 5-Flurorouracilacil (5-FU) and Leucovorin (LV) in Metastatic Colorectal Cancer Patients Resistant to 5-Fu+LV-Based Chemotherapy, Tumori, vol. 84: pp. 666-668, yr 1988.
Armstrong, DK, Fleming, GF, Markman, M et al., A phase I trial of intraperitoneal sustained-release paclitaxel microspheres (Paclimer) in recurrent ovarian cancer: a Gynecologic Oncology Group study. Gynecol. Oncol., yr 2006, pp. 391-396, vol. 103.
Chen, D, Song, D, Wientjes, MG et al., Effect of dimethyl sulfoxide on bladder tissue penetration of intravesical paclitaxel. Clin. Cancer Res., yr 2003, pp. 363-369, vol. 9.
Demetrick, JS, Liggins, RT, Machan, L et al., The development of a novel intraperitoneal tumor-seeding prophylactic. Am. J. Surg., yr 1997, pp. 403-406, vol. 173.
Ensminger, WD, and Gyves, JW, Regional chemotherapy of neoplastic diseases. Pharmacol. Ther., yr 1983, pp. 277-293, vol. 21.
Harper, E, Dang, W, Lapidus, RG et al., Enhanced efficacy of a novel controlled release paclitaxel formulation (Paclimer delivery system) for local-regional therapy of lung cancer tumor nodules in mice. Clin. Cancer Res., yr 1999, pp. 4242-4248, vol. 5.
Kiguchi, K, Kubota, T, Aoki, D et al., A patient-like orthotopic implantation nude mouse model of highly metastatic human ovarian cancer. Clin. Exp. Metastasis, yr 1998, pp. 751-756, vol. 16.
Machida, Y, Onishi, H, Kurita, A et al., Pharmacokinetics of prolonged-release CPT-11-loaded microspheres in rats. J. Control Release, yr 2000, pp. 159-175, vol. 66.
Markman, M, Rowinsky, E, Hakes, T et al., Phase I trial of intraperitoneal taxol: a Gynecoloic Oncology Group study. J. Clin. Oncol., yr 1992, pp. 1485-1491, vol. 10.
Rasband, W. S. ImageJ. Http://Rsb.Info.Nih.Gov/lj/. 2008. NIH.
Tokuda, K, Natsugoe, S, Shimada, M et al., Design and testing of a new cisplatin form using a base material by combining poly-D,L-lactic acid and polyethylene glycol acid against peritoneal metastasis. Int. J. Cancer, yr 1998, pp. 709-712, vol. 76.
Tsai, M, Lu, Z, Wang, J et al., Effects of carrier on disposition and antitumor activity of intraperitoneal Paclitaxel. Pharm. Res, yr 2007, pp. 1691-1701, vol. 24.

* cited by examiner

*Primary Examiner* — Brandon Fetterolf
*Assistant Examiner* — Shirley V Gembeh
(74) *Attorney, Agent, or Firm* — Mueller Smith & Okuley, LLC

(57) ABSTRACT

A composition for delivering a tumor therapeutic agent to a patient includes a fast-release formulation of a tumor apoptosis inducing agent, a slow-release formulation of a tumor therapeutic agent, and a pharmaceutically acceptable carrier. An apoptosis-inducing agent in a pharmaceutically acceptable carrier may be administered before or concomitantly therewith. Nanoparticles or microparticles (e.g., cross-linked gelatin) of the therapeutic agent (e.g., paclitaxel) also may be used. The nanoparticles or microparticles may be coated with a bioadhesive coating. Microspheres that agglomerate to block the entrance of the lymphatic ducts of the bladder to retard clearance of the microparticles through the lymphatic system also may be employed. This invention also uses drug-loaded gelatin and poly(lactide-co-glycolide) (PLGA) nanoparticles and microparticles to target drug delivery to tumors in the peritoneal cavity, bladder tissues, and kidneys.

36 Claims, 6 Drawing Sheets

TUMOR TARGETING DRUG-LOADED PARTICLES

GOVERNMENT SPONSORED RESEARCH

This work was supported, in part, by a grant from the U.S. Department of Health and Human Services (Grant number R37CA49816).

RELATED INFORMATION

This application claims priority to PCT/US2004/010230, filed on Apr. 2, 2004; and to provisional application Ser. No. 60/460,827 filed on Apr. 3, 2003, the disclosures of both applications being hereby incorporated by reference in their entireties.

OVERVIEW OF THE INVENTION

Successful chemotherapy of cancer requires delivering sufficient concentrations of an effective drug to tumor cells without causing intolerable toxicity to the patient. The present invention describes two drug-loaded particles designed to target tumors. The first is drug-loaded microparticles for the treatment of peritoneal cancers, where the particles are administered intraperitoneally to the peritoneal cavity. These particles also can be administered locally to other tumor-bearing organs. The second is drug-loaded nanoparticles for the intravesical treatment of bladder cancer; where the particles are administered intravesically to the bladder cavity. The nanoparticles also can be administered systemically to target the kidney.

BACKGROUND OF THE INVENTION

Drug-Loaded Microparticles

Multiple types of cancer originate from organs located within the peritoneal cavity, e.g., pancreatic, liver, colorectal, and ovarian cancer. The peritoneal cavity also is a site for metastasis of cancer originating from organs outside of the peritoneal cavity during the late stage of disease, e.g., lung cancer. Within the peritoneal cavity, tumors can be found in pelvic and abdominal peritoneal surfaces, other peritoneal organs, e.g., intestinal mesenteries, bladder, omentum, diaphragm, lymph nodes and liver. Obstruction of the diaphragmatic or abdominal lymphatic drainage by tumor cells leads to decreased outflow of peritoneal fluid resulting in carcinomatosis or ascites.

Intraperitoneal chemotherapy, where the drug is directly instilled into the peritoneal cavity, has been used to treat peritoneal cancer, e.g., advanced ovarian and colon cancer (Otto, S. E., *J Intraven. Nurs.*, 18:170-176, 1995; Collins, J. M., *J Clin Oncol*, 2:498-504, 1984). Intraperitoneal administration of platinated compounds, e.g., cisplatin, and Taxol®, the commercially available formulation of paclitaxel, has produced some benefits in patients and extended the survival time by about 20% (Gadducci, et al., *Gynecol Oncol* 76:157-162, 2000; Markman, et al. *J Clin Oncol*, 19:1001-1007, 2001). However, intraperitoneal chemotherapy has the following drawbacks that limit its use. Intraperitoneal treatments are usually administered through indwelling catheters, every 3 weeks for 6 treatments. The two major side effects are infection associated with the prolonged use of a catheter and abdominal pain due to the presentation of high drug concentrations in the peritoneal cavity (Francis, et al., *J Clin Oncol*, 13:2961-2967, 1995). Further, intraperitoneal administration requires hospitalization and is associated with substantial costs. These reasons have contributed to the reluctance of the medical community to use intraperitoneal treatments in spite of its demonstrated survival benefits. The current invention overcomes these various deficiencies.

In an earlier invention (U.S. patent application Ser. No. 09/547,825), Applicants showed that when anticancer drugs (e.g., paclitaxel, doxorubicin) are administered to the exterior of a solid tumor, as would be the case during regional intraperitoneal therapy, the drug penetration into solid tumors is very slow and limited to the tumor periphery. Applicants further disclosed a method to overcome this penetration problem. This method consists of using an apoptosis induction treatment (e.g., treatment with paclitaxel or doxorubicin) to expand the interstitial space within a tumor and thereby improve the penetration and distribution throughout solid tumors of the concurrently and subsequently administered drugs. This method is referred to as the "Tumor Priming" method in the current application, and has two requirements. The first requirement is that the drug concentrations must be sufficient to induce apoptosis. Applicants have shown that treatment with 200 nM paclitaxel for 3 hours is sufficient to induce apoptosis in multiple human tumor cells (Au, et al., *Cancer Res.*, 58:2141-2148, 1998). The second requirement is that the time interval between the apoptosis-inducing pretreatment and subsequent treatments must be sufficient to allow apoptosis to occur, e.g., 16-24 hours for paclitaxel (Au, et al., *Cancer Res.*, 1998; Jang, et al., *J. Pharmacol. Exper. Therap.*, 296:1035-1042, 2001). These requirements are captured in the current invention.

Applicants further discovered that after intraperitoneal administration, the commercial Taxol® formulation was rapidly cleared from the peritoneal cavity, due to rapid absorption through the peritoneum, a thin membrane lining the peritoneal cavity, and due to drainage through the lymphatic system (see Examples 4 and 6, infra).

Based on these various considerations and discoveries, Applicants arrived at the conclusion that therapeutically useful intraperitoneal chemotherapy can be accomplished, if the treatment satisfies some or most of the following desired properties. First, the drug should have activity against the intended target cancer type. Second, the treatment should be easy to administer, does not require the use of indwelling catheter over long period of time, e.g., longer than one day or two days, and does not require frequent administration, e.g., no more than once a week. Third, the rate of drug presentation should be optimized so that the drug amount and, therefore, the drug concentration in the peritoneal cavity is high enough to provide adequate control of the disease but at the same time low enough to not produce significant local toxicity. Fourth, the drug or drug formulation must be able to penetrate into and widely distribute within solid tumors. Fifth, the drug or drug formulation should have a long retention in the peritoneal cavity where the tumors are located. Sixth, the drug or drug formulation should have high affinity to tumor cells and localize on tumor surface or within the tumor mass. Seventh, the distribution of the drug or drug formulation should be similar to the distribution or dissemination of tumor cells, within the peritoneal cavity or organs. Most or all of these desired features are captured in the current invention, i.e., drug-loaded microparticles.

The drug-loaded microparticles are designed to release the drug at two rates; a rapid release to provide sufficiently high drug concentration to induce apoptosis and a slower release to provide sustained drug delivery to tumors. The apoptosis induction promotes the penetration and distribution of the remaining microparticles and the remaining drug subsequently released from the slow-release particles. The slow drug release over a long time period, e.g., days, weeks or months, offers the patient the convenience of a single administration, reduces the frequency of treatments, eliminates the need of hospitalization, reduces the health care costs, eliminates the need of using indwelling intraperitoneal catheters and thereby reduces the risk of infections and improves the quality of life for a patient, and reduces the local toxicity due to the high local concentrations in the peritoneal cavity resulting from rapid bolus presentation of the entire dose all at once. These particles, due to their sizes and properties, are retained in the peritoneal cavity, adhere to tumors, and show similar distribution within the peritoneal cavity or organs.

The particles also can be combinations of two or more types of particles, with at least one type releasing the drug rapidly to induce apoptosis while the remaining types release the drug more slowly. Examples of microparticles loaded with a widely used anticancer drug paclitaxel are provided to demonstrate the utility of these particles, with respect to producing superior tumor targeting and antitumor activity in mice bearing peritoneal tumors, as compared to the commercial paclitaxel formulation, i.e., Taxol®, where paclitaxel is solublilized in Cremophor and ethanol.

Applicants further disclose that other drugs or agents can be formulated in the same microparticles for the purpose of treating peritoneal cancer.

Applicants further describe that drug-loaded particles can be used to treat tumors located in organs or regions that are readily accessible by local or regional administration.

The current invention uses biodegradable particles made of gelatin and PLGA polymers, loaded with agents of therapeutic utility. One of the agents formulated in the gelatin and PLGA particles is paclitaxel. A variety of biodegradable polymer bound paclitaxel formulations have been developed and have been shown to inhibit tumor growth and angiogenesis in animal models with minimal systemic toxicity; however, the release kinetics of paclitaxel in these systems, which range from about 10-25% of the drug released in approximately 50 days, are, most likely, not optimal for clinical use (U.S. Pat. No. 6,447,796). In addition, the purpose of most of these earlier studies was to achieve systemic, rather than regional, delivery of the drug. The advantages of biodegradable polymers as a carrier for agents of therapeutic utility are art-recognized (U.S. Pat. No. 6,447,796), and include: (1) complete biodegradation, requiring no follow-up surgery to remove the drug carrier when the drug supply is exhausted; (2) tissue biocompatibility; (3) ease of administration; (4) controlled, sustained release of the encapsulated drug upon hydrolysis of the polymer; (5) in case of regional use, minimization or elimination of systemic toxicity, such as neutropenia; and (6) the convenience of the biodegradable polymer system itself, in terms of versatility. Many of these advantages, similarly, apply to gelatin drug release particles.

Paclitaxel-Loaded Nanoparticles for Intravesical Therapy of Bladder Cancer

Intravesical chemotherapy is used to reduce bladder cancer recurrence and/or progression (Kurth, K. H., *Semin. Urol. Oncol.*, 14: 30-35, 1996). Intravesical chemotherapy provides the advantage of selectively delivering drugs in high concentration to the tumor-bearing bladder, while minimizing the systemic exposure. Applicants have shown that treatment failure in superficial bladder cancer patients to chemotherapy, e.g., mitomycin C, e.g., doxorubicin, is in part due to the low drug delivery to tumors located in the bladder tissue (Dalton, et al., *Cancer Res.*, 51: 5144-5152, 1991; Schmittgen, et al., *Cancer Res.*, 51: 3849-3856, 1991; Wientjes, et al., *Pharm. Res.*, 8: 168-173, 1991; Wientjes, et al., *Cancer Res.*, 51: 4347-4354, 1991; Wientjes, et al., *Cancer Res.*, 53: 3314-3320, 1993; Chai, et al., *J Urol.*, 152: 374-378, 1994; Wientjes, et al., *Cancer Chemother Pharmacol.* 37: 539-546, 1996; Au, et al., *J. Natl. Cancer Inst.*, 93: 597-604, 2001; U.S. Pat. No. 6,286,513 B1). The low drug delivery, in turn, was due to several reasons. First, only a fraction of the mitomycin C or doxorubicin dose, e.g., ~3% to ~5%, was able to penetrate the urothelium that lines the inner surface of the bladder cavity. Second, the concentration of the drug was diluted by the presence of residual urine when the drug was administered and by the urine produced during the treatment interval, e.g., 2 hours. Third, the total exposure of tumor cells to the drug, e.g., mitomycin C, was restricted to the length of the treatment interval due to the patient's need to empty his or her bladder. Fourth, the residence of the drug, e.g., mitomycin C, in the bladder tissue is dictated by the treatment duration and is largely terminated within minutes after the patient empties his or her bladder.

Based on these various considerations and discoveries, Applicants arrived at the conclusion that therapeutically useful intravesical chemotherapy can be accomplished, if the treatment satisfies some or most of the following desired properties. First, the drug should have activity against bladder cancer. Second, a large fraction of the drug present in the urine must be able to penetrate the urothelium. Third, the residence time of the drug in the bladder tissues should exceed the duration of the treatment. Fourth, the drug concentration in the urine should be independent of the urine volume. Paclitaxel is active against bladder cancer (Roth, B., *J. Semin. Oncol.*, 22: 1-5, 1995) and, as shown by Applicants, readily partitioned across the urothelium, e.g., 50% of the dose (Song, et al., *Cancer Chemother. Pharmacol.*, 40: 285-292, 1997). Applicants further discovered that paclitaxel is retained in tumor cells after removing drug from the extracellular matrix (Kuh, et al., *J. Pharmacol. Exp. Ther.*, 293: 761-770, 2000), a property that offers the opportunity of extending drug action beyond the 2 hour treatment duration. However, the commercial paclitaxel formulation, e.g., Taxol®, is not useful, because the Cremophor used to solubilize paclitaxel, by entrapping paclitaxel in micelles, reduces the free fraction of paclitaxel and consequently lowers the drug penetration into the bladder tissue (Knemeyer, et al., *Cancer Chemother. Pharmacol.*, 44: 241-248, 1999).

Applicants, therefore, invented paclitaxel-loaded nanoparticles that satisfy all of the desired properties identified in Applicants' discoveries. These nanoparticles release a significant fraction of the drug load within the 2-hour treatment interval, such that the paclitaxel concentration in the tissue is sufficient to produce antitumor activity in human bladder tumors (e.g., Example 8). The amount of paclitaxel released from the nanoparticles is limited by the drug solubility in the urine. Hence, the drug concentration in the urine remains relatively constant and is independent of the urine volume (e.g., Example 10). The paclitaxel released from the nanoparticles and penetrated into the bladder also is retained in the bladder tissues for periods extending beyond the 2-hour treatment duration (e.g., Example 8). Finally, Applicants determined that the nanoparticles were effective against naturally occurring bladder cancer in pet dogs (e.g., Example 10).

Applicants also disclose a method to modify the drug-loaded nanoparticles to prolong the retention of these particles in the bladder cavity or bladder tissues beyond the treatment duration, e.g., by coating the gelatin framework with bioadhesive molecules (e.g., Example 7).

Applicants further disclose that other lipophilic compounds can be formulated in the same gelatin nanoparticles.

Finally, Applicants disclose that intravenous administration of gelatin nanoparticles resulted in increased localization of the drug contents in the kidney (e.g., Example 11). Hence, methods and compositions for selective drug delivery to the kidney are also provided.

Definitions

In order to provide a clear and consistent understanding of the invention, certain terms employed in the specification, examples, and the claims are, for convenience, collected here.

As used herein, the term "aberrant growth" refers to a cell phenotype, which differs from the normal phenotype of the cell, particularly those associated either directly or indirectly with a disease such as cancer.

As used herein, the term "administering" refers to the introduction of an agent to a cell, e.g., in vitro, a cell in a mammal, i.e., in vivo, or a cell later placed back in the animal (i.e., ex vivo).

As used herein, the terms "agent", "drug", "compound", "anticancer agent", "chemotherapeutic", "antineoplastic", and "antitumor agent" are used interchangeably and refer to agent(s) (unless further qualified) that have the property of inhibiting or reducing aberrant cell growth, e.g., a cancer. The foregoing terms are also intended to include cytotoxic, cytocidal, or cytostatic agents. The term "agent" includes small molecules, macromolecules (e.g., peptides, proteins, antibodies, or antibody fragments), and nucleic acids (e.g., gene therapy constructs, recombinant viruses, nucleic acid fragments (including, e.g., synthetic nucleic acid fragments).

As used herein, the term "apoptosis" refers to any non-necrotic, well-regulated form of cell death, as defined by criteria well established in the art.

As used herein, the terms "benign", "premalignant", and "malignant" are to be given their art recognized meanings.

As used herein, the terms "cancer", "tumor cell", "tumor", "leukemia", or "leukemic cell" are used interchangeably and refer to any neoplasm ("new growth"), such as a carcinoma (derived from epithelial cells), adenocarcinoma (derived from glandular tissue), sarcoma (derived from connective tissue), lymphoma (derived from lymph tissue), or cancer of the blood (e.g., leukemia or erythroleukemia). The term cancer or tumor cell is also intended to encompass cancerous tissue or a tumor mass which shall be construed as a compilation of cancer cells or tumor cells. In addition, the term cancer or tumor cell is intended to encompass cancers or cells that may be either benign, premalignant, or malignant. Typically a cancer or tumor cell exhibits various art recognized hallmarks such as, e.g., growth factor independence, lack of cell/cell contact growth inhibition, and/or abnormal karyotype. By contrast, a normal cell typically can only be passaged in culture for a finite number of passages and/or exhibits various art recognized hallmarks attributed to normal cells (e.g., growth factor dependence, contact inhibition, and/or a normal karyotype).

As used herein, the term "cell" includes any eukaryotic cell, such as somatic or germ line mammalian cells, or cell lines, e.g., HeLa cells (human), NIH3T3 cells (murine), embryonic stem cells, and cell types such as hematopoietic stem cells, myoblasts, hepatocytes, lymphocytes, and epithelial cells and, e.g., the cell lines described herein.

As used herein, the terms "peritoneal", "intraperitoneal", "peritoneally", or "intraperitoneally" are used interchangeably, and are related to the peritoneal or abdominal cavity.

As used herein, the terms "locally", "regionally", "systemically" refer to, respectively, the administration of a therapy "locally", e.g., into a tumor mass, "regionally", e.g., in a general tumor field or area suspected to be seeded with metastases, or "systemically" e.g., orally or intravenously with the intent that the agent will be widely disseminated throughout the subject.

As used herein, the term "pharmaceutically acceptable carrier" is art recognized and includes a pharmaceutically acceptable material, composition or vehicle, suitable for administering compounds of the present invention to mammals.

As used herein, the term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient (e.g., a therapeutically-effective amount) in combination with a pharmaceutically acceptable carrier.

As used herein, the term "subject" is intended to include human and non-human animals (e.g., mice, rats, rabbits, cats, dogs, livestock, and primates). Preferred human animals include a human patient having a disorder characterized by aberrant cell growth, e.g., a cancer.

As used herein, the term "microparticles" refers to particles of about 0.1 µm to about 100 µm about 0.5 µm to about 50 µm, 0.5 µm to about 20 µm in size, advantageously, particles of about 1 µm to about 10 µm in size, about 5 µm in size, or mixtures thereof. The microparticles may comprise macromolecules, gene therapy constructs, or chemotherapeutic agents, for example. Typically microparticles can be administered locally or regionally, for example.

As used herein, the term "nanoparticles" refers to particles of about 0.1 nm to about 1 µm, 1 nm to about 1 µm, about 10 nm to about 1 µm, about 50 nm to about 1 µm, about 100 nm to about 1 µm, about 250-900 nm in size, or, advantageously, about 600-800 nm. The nanoparticles may comprise macromolecules, gene therapy constructs, or chemotherapeutic agents, for example. Typically, nanoparticles can be administered to a patient via local, regional, or systemic administration.

As used herein, the term "particles" refers to nanoparticles, microparticles, or both nanoparticles and microparticles.

As used herein, the term "formulation" refers to the art-recognized composition where a therapeutically active agent is incorporated in a dosage form.

As used herein, the terms "fast-release formulation" and "rapid-release formulation" refer to a formulation of a drug which releases preferably >10%, more preferably >20%, more preferably >30%, more preferably >40%, more preferably >50%, and even more preferably >60% of its drug contents within one day. Examples of fast-release formulations include microparticle and nanoparticle formulations. Methods used to prepare these formulations are described in Examples 3 and 7.

As used herein, the term "slow-release formulation" refers to a formulation of a drug wherein the drug is delivered to a site of interest for a sustained period of time and includes formulations which maintain release of its drug contents preferably for several days, more preferably several weeks or longer.

As used herein, the term "tumor priming method" refers to a method of enhancing the penetration of a therapeutic drug by "priming" the tumor with an apoptosis inducing agent to decrease tumor cell density and increase therapeutic agent accessibility to the tumor mass. This method involves the use of an apoptosis inducing agent, such as paclitaxel, in doses and for periods of time sufficient to cause apoptosis in the tissue to thereby allow for enhanced penetration of the tumor therapeutic agent (or simply "therapeutic agent") into the tissue (e.g., by creating channels within the tissues). Thus, the apoptosis inducing agent is used as a pretreatment before the therapeutic dose of the therapeutic agent is delivered to the tissue, and this pretreatment allows for enhanced penetration of the therapeutic agent into the tissue as compared to when the pretreatment is not used. The apoptosis inducing agent may also have therapeutic activity and thus may also be used as the therapeutic agent (i.e., the same drug may be used as the apoptosis inducing agent and the therapeutic agent). Alternatively, the apoptosis inducing agent may be used to enhance delivery of other types of drugs or vehicles for treatment into tissues (i.e., the apoptosis inducing agent and the therapeutic agent may be different drugs, or the therapeutic agent may be contained in nanoparticles or microparticles, where the delivery of the nanoparticles or microparticles to the tumor tissue is enhanced, compared to when the pretreatment is not used).

As used herein, the term "PLGA", or "poly(lactide-co-glycolide)" refers to a copolymer consisting of various ratios of lactic acid or lactide (LA) and glycolic acid or glycolide (GA). The copolymer can have different average chain lengths, resulting in different internal viscosities and differences in polymer properties. PLGA is used for the preparation of microparticles or nanoparticles, usually containing therapeutic agents. Methods used to prepare these particles are described in Example 3.

As used herein, the term "gelatin" refers to a denatured form of the connective tissue protein collagen. Gelatin aggregates, formed in solution, are stabilized by cross-linking the protein chains. Using the preparation method of Example 7, gelatin forms gelatin nanoparticles, usually loaded with paclitaxel. Gelatin is available in different protein chain lengths, indicated by different Bloom numbers. Larger Bloom numbers indicate longer chain lengths.

As used herein, the term "$IC_{50}$" refers to the drug concentration or dose that results in 50% of the drug effect.

As used herein, the term "burst release" refers to the art-recognized definition of the initial, rapid release of a fraction of the drug load from a formulation, which is typically followed by a slower release of the remainder of the drug load.

As used herein, the terms "localize" and "concentrate" are used interchangeably, to indicate the preferential distribution at a specific site, e.g., tumor tissues.

As used herein the term "bioadhesive" means natural, synthetic or semi-synthetic substances that adhere and preferably strongly adhere to a surface such as skin, mucous membrane, and tumor. Suitable bioadhesives include poly(lysine), fibrinogen, those prepared from partially esterified polyacrylic acid polymers, including polyacrylic acid polymers, natural or synthetic polysaccharides such as cellulose derivatives including methylcellulose, cellulose acetate, carboxymethylcellulose, hydroxyethylcellulose, pectin, and a mixture of sulfated sucrose and aluminum hydroxide.

As used herein, the term "interstitial cystitis" refers to the art-recognized medical condition of chronic, painful inflammatory condition of the bladder wall. As used herein, the terms "biodegradable" or "bioerodible" polymer refer to polymers that can degrade into low molecular weight compounds, which are known to be involved normally in metabolic pathways. The terms also include polymer systems which can be attacked in the biological milieu so that the integrity of the system, and in some cases of the macromolecules themselves is affected and gives fragments or other degradation by-products which can move away from their site of action, but not necessarily from the body.

Broad Statement of the Invention

A composition for delivering a tumor therapeutic agent to a patient, which includes a fast-release formulation of a tumor apoptosis inducing agent, a slow-release formulation of a tumor therapeutic agent, and a pharmaceutically acceptable carrier. An apoptosis inducing agent in a pharmaceutically acceptable carrier may be administered before or concomitantly therewith. Nanoparticles or microparticles (e.g., cross-linked gelatin) of the therapeutic agent (e.g., paclitaxel) also may be used. The nanoparticles or microparticles may be coated with a bioadhesive coating. Microspheres that aggregate to block the entrance of the lymphatic ducts of the bladder to retard clearance of the microparticles through the lymphatic system also may be employed.

This invention also uses drug-loaded gelatin and poly(lactide-co-glycolide) (PLGA) nanoparticles and microparticles to target drug delivery to tumors in the peritoneal cavity, bladder tissues, and kidneys.

Mice were implanted with intraperitoneal murine pancreatic Panc02 xenograft tumors by intrasplenic injection. Seven days later, tumor metastasis in the peritoneal cavity was established, and an intraperitoneal dose of PLGA microparticles containing 22.5 mg/kg paclitaxel was administered to induce tumor priming. At the indicated number of days after tumor priming, the animals received an intravenous injection of an adenoviral gene construct, transducting the gene for green fluorescent protein (Ad-GFP). Two days later, animals were euthanized, and tumors were excised. The efficacy of transduction was expressed as relative fluorescence units (RFU) per microgram protein. Note the increase in transfection for days 2 and 5 ($p<0.01$), indicating improved delivery after tumor priming.

Figure 2:
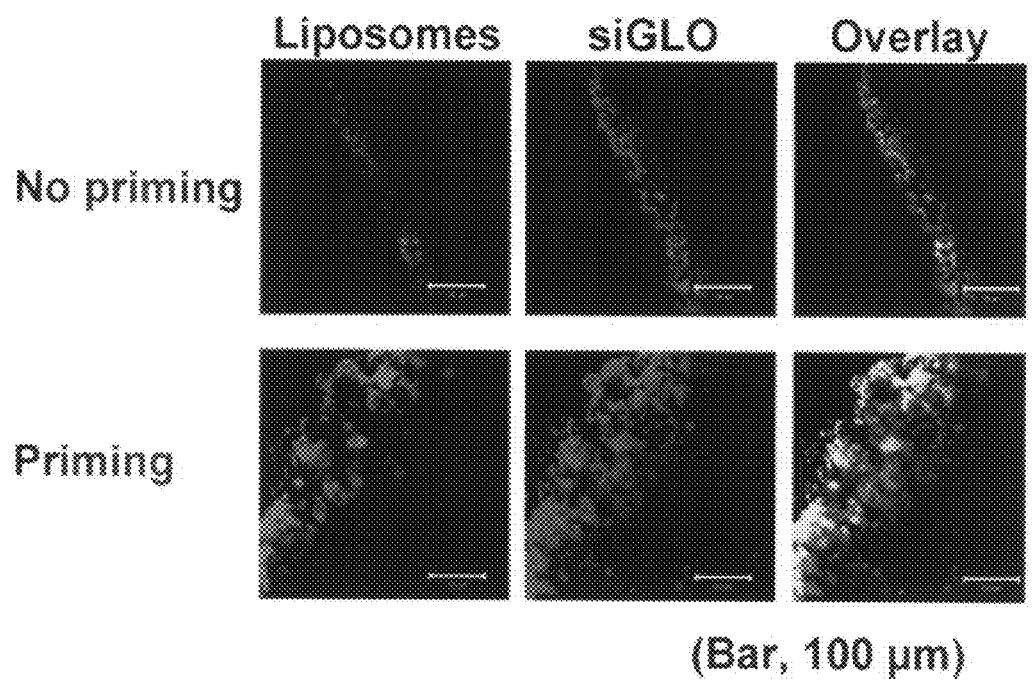

FIG. 2. Tumor Priming Promotes Lipo-SiRNA Penetration into Tumor Histocultures, In Vitro.

Histocultures of head and neck FaDu xenograft tumors were maintained in vitro. Penetration of siRNA, formulated in cationic liposomes, was evaluated with and without tumor priming pretreatment. To facilitate detection, siRNA were labeled with green fluorescence (siGLO) and lipids were labeled with a red fluorescence marker. Tumor priming was with a paclitaxel concentration of 0.5 μM, maintained for 48 hour. In the overlay picture, the red and green fluorescent images are combined. Yellow color indicates colocalization of lipids and siGLO and shows the siRNA that is contained in the cationic liposomes. Penetration of siGLO-loaded liposomes in histocultures in the absence of priming with paclitaxel is shallow, reaching a depth of approximately 20 μm. Penetration is at least five-fold deeper in histocultures pretreated with paclitaxel priming. The bars indicate a length of 100 μm.

Figure 3:
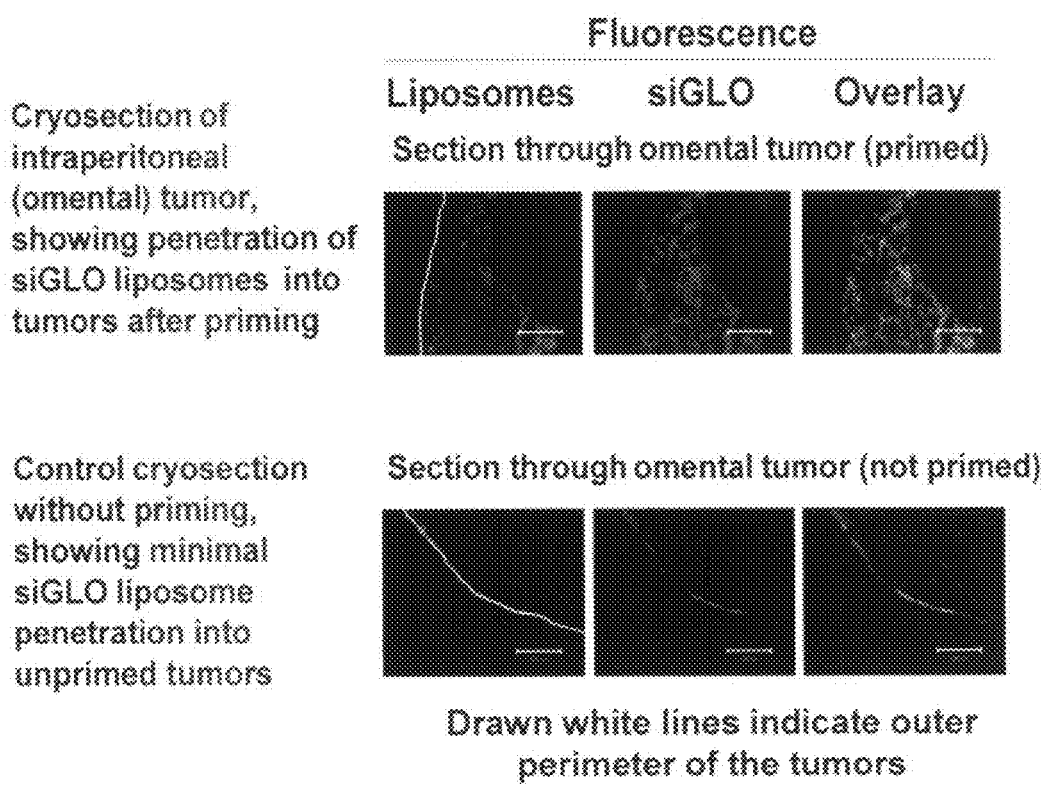

FIG. 3. Tumor Priming Promotes Lipo-SiRNA Penetration into Intraperitoneal Tumors In Vivo.

Mice were implanted with intraperitoneal human ovarian SKOV3 xenograft tumors, and were given an intraperitoneal dose of paclitaxel-loaded PLGA microparticles to induce tumor priming, after tumors were established (day 42). Two days later, the fluorescently labeled siRNA (siGLO, green fluorescence) formulated in cationic liposomes (labeled with red fluorescence) was administered intraperitoneally. One day later, animals were euthanized, and tumors were excised, frozen and cryosectioned. The localization and penetration of the liposomes and the siRNA was evaluated by fluorescence microscopy. The top panel shows penetration into the tumor tissue of the ascites tumors and omental tumors after application of tumor priming. For comparison, the bottom panel shows the minimal tumor penetration in the absence of priming. Drawn white lines indicate the outer perimeter of the tumor.

Figure 4:
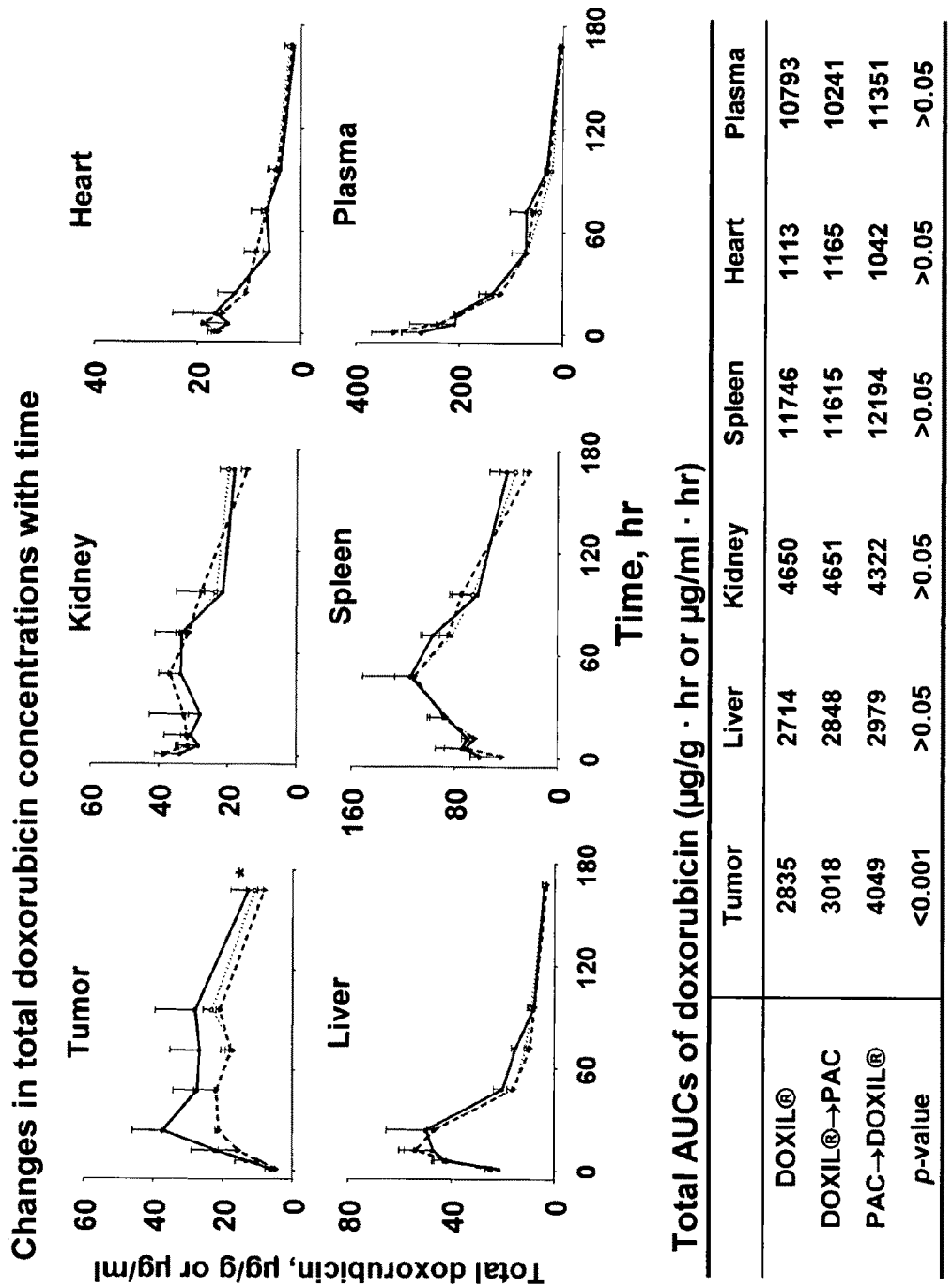

FIG. 4. Effects of Tumor Priming on Delivery of Doxorubicin-Loaded Liposomes to Tumor and Normal Tissues.

Mice were implanted subcutaneously with human head and neck FaDu xenografts, and divided in three groups when the tumors had reached a size of approximately 10 mm in diameter. The tumor priming group received the paclitaxel tumor priming treatment of 40 milligrams per kilogram administered intravenously, followed by doxorubicin HCI liposomes (20 mg per kilogram) administered 48 hours later (Priming→DOXIL®, solid circles, solid line). The two control groups were doxorubicin HCI liposomes alone (DOXIL®, triangle, dashed line), and paclitaxel plus doxorubicin HCI liposomes combination in the reversed sequence (i.e., doxorubicin HCI liposomes given 48 hours before paclitaxel: DOXIL®→Priming, open circle, dotted line). Mean + standard deviation of three to five mice per data point. The graphs show the changes in total doxorubicin concentrations with time. The units are micrograms per gram for tissues and micrograms per milliliter for plasma. Note the different scales for different tissues. Two-way ANOVA was used to compare doxorubicin concentration-time curves in tissues among treatment groups. *, $p<0.05$.

Figure 5:
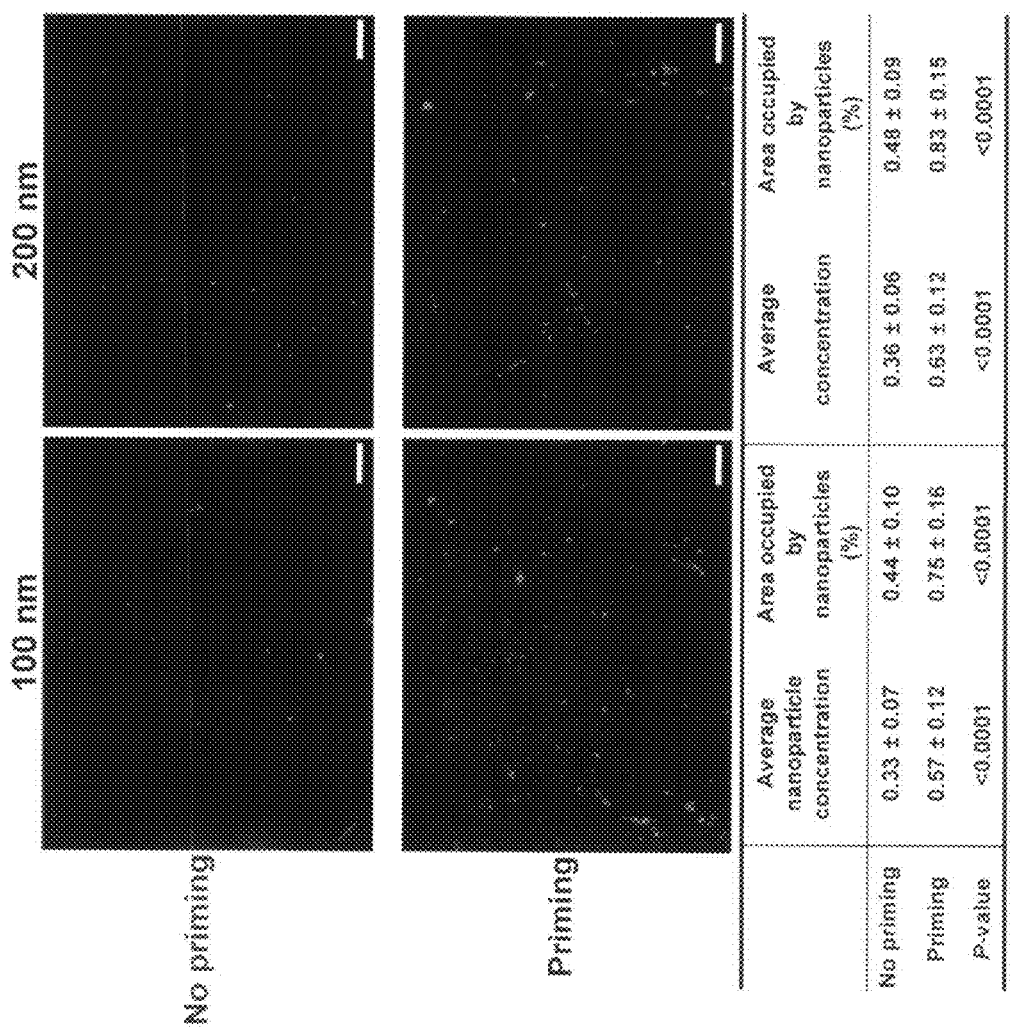

FIG. 5. Effects of Tumor-Priming on Nano-sized Latex Bead Delivery and Dispersion in Tumors.

Mice were implanted subcutaneously with human head and neck FaDu xenografts, and divided in two groups. The tumor priming group received the paclitaxel tumor priming treatment of 40 milligrams per kilogram administered intravenously in a vehicle of polyoxyethylated castor oil/ethanol. The control group (without tumor priming) only received the vehicle. Forty-eight hours later, animals received an intravenous injection of red fluorescent latex beads of 100, or 200 nm diameter. Tumors were excised 24 hours after the injection of the beads and examined. Bar, 100 μm. The table shows the results of computer-assisted image analysis of the micrographs. The percentage of area in tumors occupied by particles was calculated as (total number of deep-derived pixels) divided by (total number of pixels per microscopic field), which provided a measurement of the dispersion area. The average bead concentration in tumors was the average fluorescence intensity, which was calculated as (mean intensity of bead-derived pixels multiplied by total number of bead-derived pixels) divided by (total number of pixels per microscopic field). Eight tumors were used per data point. Mean ± S.D. Note that tumor priming enhanced the delivery of the 100- and 200-nm latex beads, as indicated the increase in the amount and dispersion of red fluorescent beads.

Figure 6:
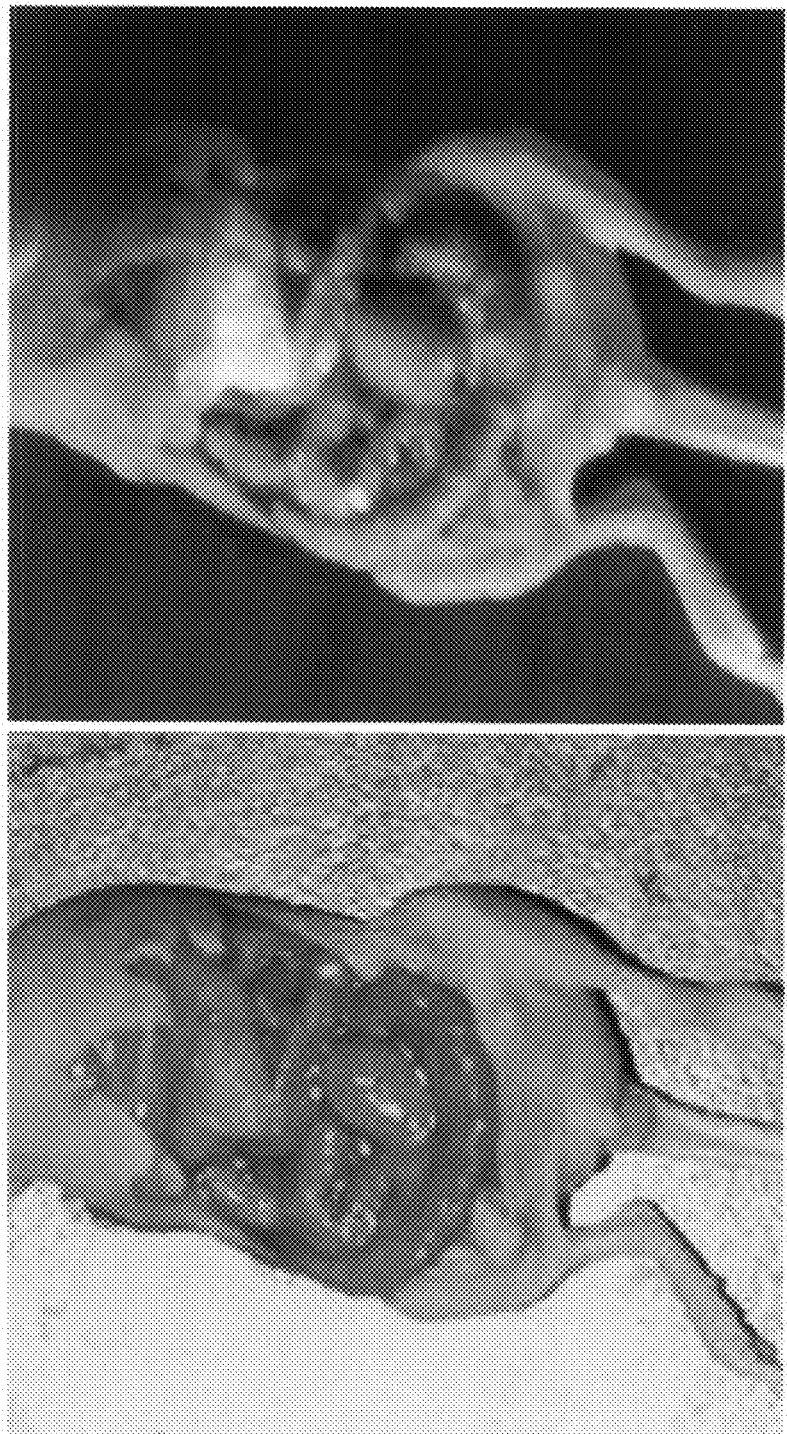

FIG. 6. Tumor Targeting by PLGA Microparticles Mice were implanted with intraperitoneal human ovarian SKOV3 xenograft tumors. After tumors were established (day 42), a mouse was given an IP dose of rhodamine-labeled tumor priming microparticles composed of PLGA with 50% lactide and 50% glycolide. Three days after treatment, the animal was anesthetized and the abdominal cavity was exposed. Left panel: Room light. Note the multiple tumors, appearing as whitish/yellowish and irregular shaped nodules, disseminated through the peritoneal cavity. Right panel: UV light. The particles (red color) were localized on tumor nodules.

DETAILED DESCRIPTION OF THE INVENTION

This invention provides methods, and compositions used therein, for delivering therapeutic agents to tumor and kidney tissues, wherein the methods allow for enhanced targeting and enhanced penetration of the therapeutic agents into the interior of multilayered tissues, such as solid tissues or tumors.

In a first aspect, this invention provides a method to promote the penetration of a chemotherapeutic agent or particles into a tumor. This method involves the use of apoptosis inducing agents, such as paclitaxel, in doses and for periods of time sufficient to cause apoptosis in the tissue. Subsequent delivery of therapeutic agents or particles into the tissue, at a time when substantial apoptosis has occurred, results in enhanced penetration of the therapeutic agent or particles into the tissue. Thus, the apoptosis inducing agent is used as a pretreatment before the therapeutic agent or particles is delivered to the tissue, and this pretreatment allows for enhanced penetration of the therapeutic agent or particles into the tissue as compared to when the pretreatment is not used. The apoptosis-inducing agent also may have therapeutic activity and, thus, may also be used as the therapeutic agent (i.e., the same drug may be used as the apoptosis inducing agent and the therapeutic agent). Alternatively, the apoptosis inducing agent may be used to enhance delivery of other types of drugs into tissues (i.e., the apoptosis inducing agent and the therapeutic agent may be different drugs).

In one embodiment, the invention uses formulations which allow for the concomitant administration of the apoptosis-inducing agent and the therapeutic agent. In this embodiment, the apoptosis inducing agent is formulated as a fast-release formulation, and the therapeutic agent is formulated in one or more slow-release formulations. After administration, the rapid formulation will result in apoptosis in the tissue and the slow-release formulation will allow for delivery of most of the total amount of the therapeutic agent after a substantial degree of apoptosis has been achieved.

In a related embodiment, the formulation is a single formulation which provides an initial burst release of the apoptosis-inducing agent, followed by a slower release of the remaining drug load which serves as the therapeutic agent.

In a related embodiment, the formulations described above will be used for the treatment of tumors in the peritoneal cavity and in tissues adjoining the peritoneal cavity.

In a further related embodiment, the combined formulation described above will be used for the treatment of ascites tumors.

In yet a further related embodiment, these formulations are used to treat a metastatic tumor from any origin, which grows in the abdominal cavity or in tissues adjacent to the abdominal cavity where the tumor protrudes into the abdominal cavity.

In a related embodiment, these formulations are used to treat a tumor located in organs or regions that are readily accessible by direct administration, e.g., in one or more of tissues within or adjacent to the peritoneal cavity, bladder tissue, brain tissue, prostrate tissue, or lung tissue, In another embodiment, the tumors to be treated are in the abdominal cavity of a subject or grow in a tissue adjacent to the abdominal cavity.

In a related embodiment, the tumors to be treated are located in organs or regions that are readily accessible by direct administration, e.g., prostate, bladder, brain.

In a further embodiment, the microparticles are delivered as a suspension by the intraperitoneal route.

In another embodiment, the microparticles are delivered as a suspension by direct local injection into a readily accessible organ or by direct regional injection adjacent to a readily accessible organ.

In yet a further embodiment, the subject is a mammal, preferably a human.

In another embodiment, the patient to be treated is a patient that suffers from a pancreatic cancer or ovarian cancer, which has spread to the abdominal cavity.

In a second aspect, this invention provides for compositions to be used in the above method. These compositions consist of various drug-loaded PLGA particles that release the apoptosis-inducing agent and the therapeutic agent over time, and that provide for an initial rapid release of the apoptosis-inducing agent, followed by a slower release of the therapeutic agent.

In a particular embodiment, the formulation consists of a fast-release component, which releases preferably >10%, more preferably >20%, more preferably >30%, more preferably >40%, more preferably >50%, and even more preferably >60% of its contents of an apoptosis-inducing agent within one day and causes apoptosis in the tissue, and further consists of one or more slow-release components, which maintain release of a therapeutic agent preferably for several days, more preferably several weeks or longer.

In a related embodiment, the composition can be a single formulation of paclitaxel consisting of an initial burst release, followed by a slower release of the remaining drug load.

In a particular embodiment, the composition can also be a combination of two or more formulations of paclitaxel, where at least one formulation provides a rapid release of paclitaxel and at least one formulation provides a slower release of paclitaxel. In a related embodiment, the combined formulation provides a better controlled drug release, consisting of a rapid early release followed by a protracted later release, than can be obtained by a single formulation with an early burst release.

In yet another related embodiment, the combined formulation is especially advantageous if different agents are used as apoptosis inducing agent and as therapeutic agent.

In yet another embodiment, the particles are PLGA particles, formulated to contain the apoptosis-inducing or the therapeutic agent. A typical formulation will contain no more than 50%, preferably no more than 30% and more preferably no more than 20% of the total weight of the formulation in the form of the agent. At times, it is advantageous to add a release enhancer, such as Tween 20, Tween 80, isopropyl myristate, β-lactose, or diethylphthalate, in order to achieve a release rate as desired for the application.

In a preferred embodiment, the fast-release PLGA microparticles are made of 50:50 LA:GA, have an average diameter of between 3 to 5 μm, a glass transition temperature that is below the body temperature (e.g., 30° C.), a ~4% load of paclitaxel, and a drug release rate of ~70% in one day. An example of this composition is Batch 8 described in Table 1.

In a preferred embodiment, the slow-release PLGA microparticles are made of 50:50 LA:GA, have an average diameter of between 30 to 50 μm, a glass transition temperature that is below the body temperature (e.g., 30° C.), a ~4% load of paclitaxel, and an initial burst drug release rate of ~20% in the first day, followed by a slower release yielding a total cumulative release of 70% in seven weeks. An example of this composition is Batch 7 described in Table 1.

In a preferred embodiment, the slow-release PLGA microparticles are made of 75:25 LA:GA, have an average diameter of between 3 to 5 μm, a glass transition temperature that is above the body temperature (e.g., 50° C.), a ~4% load of paclitaxel, and an initial burst drug release rate of ~5% in the first day, followed by a slower release yielding a total cumulative release of 30% in seven weeks. An example of this composition is Batch 4 described in Table 1.

In a third aspect, this invention provides for a method to achieve enhanced delivery of an agent to a tumor by administering drug-containing nanoparticles or microparticles locally where the tumor is located, where the nanoparticles or microparticles selectively adhere to the tumor tissue and thereby produce a higher drug levels in the tumor, when compared to delivery in nanoparticles or microparticles that do not selectively adhere to the tumor.

In one embodiment, the drug-containing nanoparticles or microparticles selectively adhere to the tumor tissue and, because of their release of apoptosis-inducing agent, facilitate their own penetration into the tumor. For example, the particles of Example 5 show extensive penetration into the tumor. This penetration was due to the release of the apoptosis-inducing agent, as equivalent particles not carrying an apoptosis-inducing agent did not penetrate into the tumor. After penetration into the tumor, the remainder of the drug load carried by the particle was released over time, and gave highly concentrated exposure of the tumor tissue to the released drug. The drug release rate will be impeded by the tissue surroundings, increasing the duration of exposure of the tumor tissue. Hence, the method of this embodiment, using local administration of tumor adhering particles that penetrate into the tumor tissue subsequent to an initial drug release, is an effective way of treating a tumor. Such embodiment, also, is not dependent upon the use of a fast-release or a slow-release therapeutic agent, but is applicable to the use of any therapeutic agent to treat tumor, because of the apoptosis-inducing agent carried by the particles.

In a fourth aspect, this invention provides for compositions to be used in the above method.

In one embodiment, these compositions consist of PLGA particles with a glass transition temperature (Tg) below the body temperature of the patient, thereby enhancing the selective adhesion of the particles to tumor tissue.

In a preferred embodiment, the fast release PLGA microparticles are made of about 50% lactide and about 50% glycolide, have a glass transition temperature that is below the body temperature (e.g., 30° C.). An example of such a composition is Batch 8 described in Table 1.

In a specific embodiment, the particles are formulated of PLGA containing about 50% lactide and about 50% glycolide, and are loaded with the agent, where the total weight of the agent constitutes no more than 50%, and preferably no more than 30% of the total weight of the formulation.

In another embodiment, particles that adhere to tumor tissue can be obtained by increasing their bioadhesive properties using cross-linking with poly(lysine), by coating the particles with fibrinogen, or by other art-recognized methods. These particles could be gelatin nanoparticles or PLGA microparticles.

In a fifth aspect, the invention provides for a method to achieve enhanced delivery of a drug to a tumor that has spread in the peritoneal cavity, by administering drug-containing microparticles into the peritoneal cavity, where the microparticles concentrate in the area of the peritoneal cavity where metastatic tumors most often occur, and thereby deliver higher drug levels to the tumor than if the drug is delivered in a formulation that does not concentrate in locations where metastatic tumors most often occur.

In a sixth aspect, the invention provides for compositions for the above method, i.e., PLGA microparticles, which, upon administration into the peritoneal cavity, localize in the area of the peritoneal cavity where metastatic tumors most often occur, e.g., omentum, mesentery, diaphragm and lower abdomen.

In a preferred embodiment, the PLGA microparticles have an average diameter of about 3 to 5 μm. These particles localize preferentially near the omentum, mesentery, diaphragm and lower abdomen. Examples of these compositions are Batches 4 and 8 described in Table 1.

In a preferred embodiment, the PLGA microparticles have an average diameter of about 30 to 50 µm. These particles localize preferentially in the lower abdomen. Examples of these compositions are Batches 2, 3, 5, 6, and 7 described in Table 1.

In one embodiment, the microparticles concentrate in the mesentery, on the omentum, on the diaphragm, and on other sites that are the locations of growth of metastatic peritoneal tumors.

In a related embodiment, the particles are of a size similar to the size of a single tumor cell, or a small aggregate of tumor cells, i.e., between about 3 and about 30 µm in diameter.

In a seventh aspect, the invention provides for methods to achieve enhanced retention of agent-containing microparticles in the peritoneal cavity, by formulating the agent in PLGA microparticles with a glass transition temperature (Tg) below the body temperature of the patient in order to promote the formation of aggregates of these particles and thereby reduce the clearance of these particles by the lymphatic drainage, as compared to microparticles with a Tg that is above the body temperature.

In an eighth aspect, the invention provides for compositions for the above methods, consisting of drug-loaded microparticles that have retarded lymphatic clearance.

In a preferred embodiment, the PLGA microparticles are made of about 50% lactide and about 50% glycolide and have a glass transition temperature that is below the body temperature (e.g., 30° C.). Examples of these compositions are Batches 6, 7, and 8 described in Table 1.

In a ninth aspect, the invention provides for methods to achieve enhanced retention of agent-containing microparticles in the peritoneal cavity, by formulating the agent in PLGA microparticles where the size of the particles are sufficiently large to reduce the clearance of the agent by the lymphatic drainage, as compared to when the agent is administered without being loaded into the microparticles.

In a tenth aspect, the invention provides for compositions for the above methods, consisting of drug-loaded microparticles that have sufficiently large size to retard the clearance by the lymphatic drainage.

In a preferred embodiment, the PLGA microparticles have an average diameter of at least 10 µm. Examples of these compositions are Batches 2, 3, 5, 6, and 7 described in Table 1.

In an eleventh aspect, the invention provides for methods to achieve enhanced retention of agent-containing microparticles in the peritoneal cavity, by formulating the agent in PLGA microparticles where the size of the particles reduces the clearance of the agent from the peritoneal cavity due to absorption through the peritoneal membrane, as compared to than when the agent is administered without being loaded into the micro particles.

In a twelfth aspect, the invention provides for compositions for the above methods, consisting of drug-loaded microparticles that have retarded absorption through the peritoneal membrane.

In a preferred embodiment, the PLGA microparticles have an average diameter of at least 10 µm. Examples of these compositions are Batches 2, 3, 5, 6, and 7 described in Table 1.

In a thirteenth aspect, the invention provides for compositions with at least two of the following desired properties of (1) providing a rapid drug release followed by a slow drug release, (2) adhering selectively to tumor tissue, (3) localizing in the area of the peritoneal cavity where metastatic tumors most often occur, (4) low clearance by lymphatic drainage, and (5) low absorption through the peritoneal membrane.

In a preferred embodiment, the compositions contain fast-release and slow-release PLGA particles. The fast-release PLGA particles are made of 50% lactide and 50% glycolide, have an average diameter of between 3 to 5 µm, a glass transition temperature that is below the body temperature (e.g., 30° C.), and release an apoptosis-inducing amount of an apoptosis-inducing drug within several hours. The slow-release PLGA microparticles are made of 50% lactide and 50% glycolide, have an average diameter of between 30 to 50 µm, a glass transition temperature that is below the body temperature (e.g., 30° C.), and release a therapeutic agent, releasing preferable less than 30%, and even more preferably less than 20%, of its drug load during the first day, followed by a slower release, yielding a total cumulative release of >60%, or preferably >70% in several weeks.

In an even more preferred embodiment, the apoptosis-inducing agent and the therapeutic agent are both paclitaxel.

In a fourteenth aspect, the invention provides for a method of delivering lipophilic agents to the bladder wall of a patient. This method uses gelatin nanoparticles for the formulation of the agents, where the formulation has several advantages over the administration of the free drug. Due to the formulation of the agent in gelatin nanoparticles, a larger drug amount of many poorly soluble agents can be administered than would otherwise be possible. In addition, the drug formulated in the gelatin nanoparticles serves as a reservoir for continued drug release, so that higher drug concentrations can be maintained, when compared with administration of the free agent. Further, the drug-loaded gelatin nanoparticles can be retained in the bladder cavity even when the urine is voided, thereby enhancing the total tumor exposure to the drug.

In a preferred embodiment, the invention provides a method of delivering paclitaxel to the bladder wall of a patient with a superficial bladder cancer, by intravesical instillation, where paclitaxel is not contained in a Cremophor-containing formulation, and, because of this, is more readily available for penetrating the bladder wall.

In another embodiment, other highly lipophilic agents for the treatment of superficial bladder cancer, or for the treatment of interstitial cystitis, could be administered using this method. Agents that are expected to yield improved therapeutic results using this method would include, but are not limited to, docetaxel.

In a fifteenth aspect, the invention provides for compositions to formulate paclitaxel in a delivery form suitable for intravesical instillation, where the delivery form fulfills the following criteria: (1) a sufficient dose of paclitaxel can be contained in a small volume of instillate, (2) the delivery form delivers paclitaxel rapidly and efficiently to the bladder wall, and (3) substantial and therapeutically active concentrations of paclitaxel are achieved in the bladder wall.

In one embodiment, the composition consists of cross-linked gelatin nanoparticles, loaded with paclitaxel.

In a related embodiment, the gelatin nanoparticles are formulated to provide solubility-limited release of paclitaxel, and will thus maintain the solubility concentration of paclitaxel in the urine. Because of this, a constant and effective paclitaxel concentration will be maintained independent of processes that would otherwise cause dilution and lowering of the drug concentration, including but not limited to existing residual urine at the time of drug instillation, or urine production during and after the treatment duration.

In a preferred embodiment, the gelatin nanoparticles are prepared from gelatin with bloom number of 175, have an average diameter of about 600 nm to about 1000 nm, have a 0.4% to 2.0% drug loading, and more preferably a 0.5% to 1.0% drug loading. Cross-linking of gelatin can be achieved by using glutaraldehyde as described in Example 7, or by other methods, e.g., by use of oxidized polysaccharide molecules as generally recognized in the art (U.S. Pat. No. 6,132, 759). An example of these nanoparticles is provided in Table 3 and their properties described in Example 7.

In another related embodiment, the nanoparticle formulation will further contain components to enhance the solubility of paclitaxel, and consequently increase the concentration of paclitaxel available to treat the tumor. Examples of such components are cosolvents such dimethyl sulfoxide or polyethylene glycol.

In yet another related embodiment, the solubility of paclitaxel in the urine can be increased by the application of hyperthermia.

In another embodiment, the particles adhere to the normal bladder wall, and/or to the inflamed bladder wall often observed in patients afflicted with superficial bladder cancer, and/or to the tumor tissue exposed on the surface of the bladder wall. This adherence can be increased by coating the nanoparticles with bioadhesive molecules, including, but not limited to, poly(lysine), fibrinogen, polyacrylic acid polymers, methylcellulose, cellulose acetate, carboxymethylcellulose, hydroxyethylcellulose, or pectin.

In a related embodiment, adherence of the nanoparticles to the bladder wall enables the maintenance of effective drug concentrations in the bladder cavity, even after the patient has emptied his or her bladder.

In a specific embodiment, the particles adhering to the bladder wall are gelatin nanoparticles loaded with a lipophilic therapeutic agent, and coated with bioadhesive molecules.

In a preferred embodiment, the particles are gelatin nanoparticles, loaded with paclitaxel, and coated with poly (lysine).

In an even more preferred embodiment, the gelatin nanoparticles are prepared from gelatin with a Bloom number of 175, have an average diameter of about 600 nm to about 1000 nm, a drug loading of about 0.4% to 2%, and more preferably of about 0.5% to 1%, contain 5% of their weight in poly (lysine), where the gelatin molecules, and the poly(lysine) molecules are cross-linking by using glutaraldehyde as described in Example 7, or other art-recognized cross-linking methods.

In another embodiment, the delivery form suitable for intravesical installation consists of fast-release PLGA microparticles.

In another embodiment, the release rate of the therapeutic agent into the bladder contents is limited by the aqueous solubility of the agent.

In a preferred embodiment, the agent is paclitaxel.

In another embodiment, the fast-release PLGA microparticles have an average diameter of between 100 nm and 6000 nm, preferably 500 to 5000 nm, more preferably 3000 to 4000 nm.

In a preferred embodiment, the fast-release PLGA microparticles are made of 50:50 LA:GA, have an average diameter of 3000 to 5000 nm, a glass transition temperature that is below the body temperature (e.g., 30° C.), contains approximately 4% paclitaxel, and have a drug release rate of approximately 70% of its drug contents in one day under sink conditions.

In another embodiment, the PLGA microparticles are coated with bioadhesive molecules.

In a sixteenth aspect, the invention provides for a method of increasing the delivery of an agent to the kidney, when the agent is administered by the intravenous route. This method is based on the selective distribution of gelatin nanoparticles to the kidney, as compared to the distribution of agents administered intravenously.

In one embodiment, selective targeting of kidney tissue is accomplished by intravenous administration of an agent formulated in gelatin nanoparticles.

In a preferred embodiment, the method of selective targeting of the kidney will be as described in the Example 11.

In an even more preferred embodiment, gelatin nanoparticles with an approximate average size of 600 to 900 nm, and loaded with a therapeutically useful agent, will be used to target the kidney in a subject.

In another embodiment, agents that will be formulated in gelatin nanoparticles include chemotherapy agents for the treatment of renal cancer, chemopreventive agents for the prevention of renal cancer, gene therapy constructs for the treatment of kidney diseases, and other agents for which selective administration to the kidney is beneficial.

In a seventeenth aspect, the invention provides for a composition to formulate paclitaxel, or other agents, in a delivery form suitable for selective intravenous targeting of the kidney. This composition consists of cross-linked gelatin nanoparticles, loaded with an agent to be delivered.

In a preferred embodiment, the agent is paclitaxel.

In an even more preferred embodiment, the gelatin nanoparticles are prepared from gelatin with bloom number of 175, have an average diameter of about 600 nm to about 1000 nm, have a 0.4% to 2.0% drug loading, and more preferably a 0.5% to 1.0% drug loading. Cross-linking of gelatin can be achieved by using glutaraldehyde as described in Example 7, or by other methods, e.g., by use of oxidized polysaccharide molecules as generally recognized in the art (U.S. Pat. No. 6,132,759). An example of these nanoparticles is provided in Table 3 and their properties are described in Example 7.

In another embodiment, the agent is a gene product for selective delivery of a gene construct to cells of the kidney.

In a seventeenth aspect, the invention provides for a method of delivering agents to the bladder wall of a patient. This method uses gelatin nanoparticles for the formulation of the agents, where the formulation has several advantages over the administration of the free drug. Due to the formulation of the agent in gelatin nanoparticles, a larger drug amount of agents can be administered than would otherwise be possible.

In a preferred embodiment, the drug formulated in the gelatin nanoparticles serves as a reservoir for continued drug release, so that higher drug concentrations can be maintained, when compared with administration of the free agent. Further, the drug-loaded gelatin nanoparticles can be retained in the bladder cavity even when the urine is voided, thereby enhancing the total tumor exposure to the drug.

In another embodiment, other highly lipophilic agents for the treatment of superficial bladder cancer could be administered using this method. Agents that are expected to yield improved therapeutic results using this method would include, but are not limited to, docetaxel.

In another embodiment, other agents for the treatment of superficial bladder cancer, could be administered using this method. The agents would include, but are not limited to, suramin, interferons (e.g., interferon alphar, gamma, or omega), docetaxel, doxorubicin and other anthracyclines, thiotepa, mitomycins (e.g., mitomycin C), Bacillus Calmette Guerin, cisplatin, methotrexate, vinblastine, 5-fluorouracil, leuprolide, flutamide, diethylstilbestrol, estramustine, megestrol acetate, cyproterone, flutamide, and cyclophosphamide.

In another embodiment, agents for the treatment of interstitial cystitis, could be administered using this method. Agents that are expected to yield improved therapeutic results using this method would include, but are not limited to, pentosan polysulfate and its sodium salt, antihistamines (e.g., hydroxyzine and its salts, cromolyn and its sodium salt), tricyclic antidepressant (e.g., amitriptyline, desipramine, nortriptyline, doxepin and imipramine), selective serotonin reuptake inhibitors (e.g., paroxetine), pain medication (e.g., gabapentin, clonazepam), muscle relaxants (e.g., diazepam, Baclofen), anticonvulsants (e.g., gabapentin, clonazepam), opioid analgesics (e.g., vicodin, percocet, oxycontin), other analgesics (e.g., lidocaine hydrochlorid, procaine hydrochloride, salicyl alcohol, tetracaine hydrochloride, phenazopyridine hydrochloride, acetaminophen, acetylsalicyclic acid, flufenisal, ibuprofen, indoprofen, indomethacin, naproxen, codeine, oxycodone, and fentanyl citrate), antispasmoidics (e.g., Urimax, Pyridium, Urised, flavoxate, dicyclomine, propantheline), anticholinergics (e.g., Detrol, Ditropan, Levsin, hyoscyamine), H2 blockers (e.g., Tagamet, Zantac), urinary alkalinizing agents, adrenetic blocks (e.g., Cardura, Flomax, Hytrin), leukotriene inhibitors (e.g., montelukast), and agents with miscellaneous actions (e.g., dimethyl sulfoxide, heparin, oxychlorosend and its sodium salt, silver nitrate, bacillus calmette-guerin, sodium hyaluronate, resiniferatoxin, botulinum toxic).

In another embodiment, the agents could be used to treat bladder infection, e.g., antibiotics, antifungal, antiprotozoal, antiviral and other antiinfective agents. Suitable drugs for the treatment of such infections include mitomycin, ciprofloxacin, norfloxacin, ofloxacin, methanamine, nitrofurantoin, ampicillin, amoxicillin, nafcillin, trimethoprim, sulfa, trimethoprimsulfamethoxazole, erythromycin, doxycycline, metronidazole, tetracycline, kanamycin, penicillins, cephalosporins, and aminoglycosides.

In yet another embodiment, the agents could be used to treat urge incontinence, or inflammation. Suitable drugs include, inter alia, dicyclomine, desmopressin, oxybutynin, estrogen, terodiline, propantheline, doxepin, imipramine, flavoxate, phenylpropanolamine, terazosin, praxosin, pseudoephedrine, bethanechol, anticholinergics, antispasmodic agents, antimuscarinic agents, beta-2 agonists, norepinephrine uptake inhibitors, serotonin uptake inhibitors, calcium channel blockers, potassium channel openers, and muscle relaxants can also be used. Suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide (Fujiwara Co., Japan), YM-46303 (Yamanouchi Co., Japan), lanperisone (Nippon Kayaku Co., Japan) NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In another embodiment, the agents could be used to enhance urinary bladder contractility, or to reduce retention of urine in the urinary bladder.

EXAMPLE 1

Identification of the Paclitaxel Concentration and Treatment Duration that is Active Against Human Tumor Cells The present invention describes the methods for designing and the compositions of paclitaxel-loaded particles that release cytotoxic levels of paclitaxel over durations that are sufficient to cause cytotoxicity. This example identifies the paclitaxel concentrations and treatment durations that are effective against human tumor cells.

Applicants evaluated the cytotoxicity of paclitaxel (dissolved in water, 96 hour treatment) in three human pancreatic cancer cells (PANC1, MIA-PaCa and Hs766T) and in human bladder RT4 tumor cells. Drug effect was measured using the microtetrazolium dye reduction (MTT) assay. The respective concentrations that are required to produce 50% cytotoxicity ($IC_{50}$) in these cells were 1.5, 0.7, 0.7 nM. These $IC_{50}$ values are comparable to the $IC_{50}$ of paclitaxel in human breast MCF7 and ovarian SKOV3 cancer cells (Au, et al., *Cancer Res.*, 58: 2141-2148, 1998). This data indicate that pancreatic cancer cells are highly sensitive to paclitaxel. This is surprising as intravenously administered Taxol® (paclitaxel dissolved in Cremophor and ethanol) did not show appreciable activity in advanced pancreatic cancer patients (Gebbia and Gebbia, *Eur. J. Cancer,* 32A:1822-1823, 1996; Schnall and Macdonald. *Semin. Oncol.,* 23: 220-228, 1996). The $IC_{50}$ of paclitaxel in RT4 cells was 4.0±0.4 nM (96 hour treatment).

EXAMPLE 2

Establishment of Human Pancreatic and Ovarian Xenograft Tumor Models to Test the Efficacy of Paclitaxel-Loaded Microparticles This example demonstrates the establishment of peritoneal tumor models for testing the efficacy of paclitaxel-loaded microparticles.

Applicants used human pancreatic Hs766T cells derived from a lymph node metastasis to establish orthotopic and intraperitoneal tumors in athymic mice. For orthotopical model, $2 \times 10^6$ tumor cells were implanted orthotopically into the body of the pancreas. Tumors were established after 2-3 weeks (~1.5 cm to ~2 cm in diameter). For intraperitoneal tumors, Applicants established a metastatic subline by serial re-implantation of cells collected from peritoneal washings of mice given IP injections of Hs766T cells. Re-implantation of the metastatic Hs766T cells IP in 6-week old female Balb/c mice resulted in progressive tumor spread throughout the peritoneal cavity. After 2-3 weeks, tumor nodules of ~1 cm to ~1.5 cm diameter were found on the omentum, multiple nodules of ~3 mm to ~5 mm were found on the mesentery, lower abdomen, retroperitoneal cavity, and diaphragm. Ascites tumors also were present. The animals died between 3-4 weeks.

For intraperitoneal ovarian tumor model, Applicants established a metastatic subline of human ovarian SKOV3 cells, as described for Hs766T tumors. Re-implantation of the metastatic SKOV3 cells resulted in tumor establishment on the omentum at 2 weeks, on the mesentery at 4 weeks, followed by appearance of tumors invading the parenchyma of visceral organs such as liver and kidney, and tumors residing on the diaphragm in late stage (after 6 weeks). Protein concentration in peritoneal fluid increased from 3% in normal mice to about 6% in tumor-bearing mice at 2 weeks. The volume of peritoneal fluid increased 7-10 folds after 4 weeks, and contained aggregates of tumor cells. The size of these ascites tumors ranged from 40 to several hundred µm. After 5-6 weeks, animals displayed significant body weight loss (10-15%), some mice showed peritoneal distention (20% increase in body circumferences from 6.3 cm to 7.6 cm), and intestinal obstruction. Animals died between 7-9 weeks after tumor implantation.

The disease progression in pancreatic and ovarian tumor-bearing mice is similar to that reported in patients. For example, ovarian cancer patients show similar tumor dissemination and progression in the peritoneal cavity, with tumors appearing in bowel serosa, perihepatic and perisplenic ligaments, diaphragm, mesentery, and omentum. They also show high protein concentrations in the peritoneal fluid (4.46 g/dl in late stage), due to leakage of serum proteins and/or presence of ascites in the peritoneal cavity (Lee, et al., Cancer, 70: 2057-2060, 1992). Malignant ascites in patients show tumor cell aggregates of similar sizes (Tauchi, et al., Acta Cytol., 40: 429-436, 1996; Monte, et al., Acta Cytol., 31: 448-452, 1987) as in SKOV3 ascites tumors.

EXAMPLE 3

Identifying the Effects of PLGA Microparticle Properties on their Distribution and Retention in Peritoneal Cavity This invention discloses the compositions of drug-loaded PLGA particles that target peritoneal tumors. This example demonstrates the effects of different properties of PLGA microparticles on the distribution and retention of microparticles in peritoneal cavity, to aid the identification of the PLGA microparticles with the desired retention and distribution characteristics. Examples 4 through 6 describe the preparation and application of such drug-loaded PLGA microparticles, using paclitaxel, a widely used anticancer drug, as an example.

Figure 1:
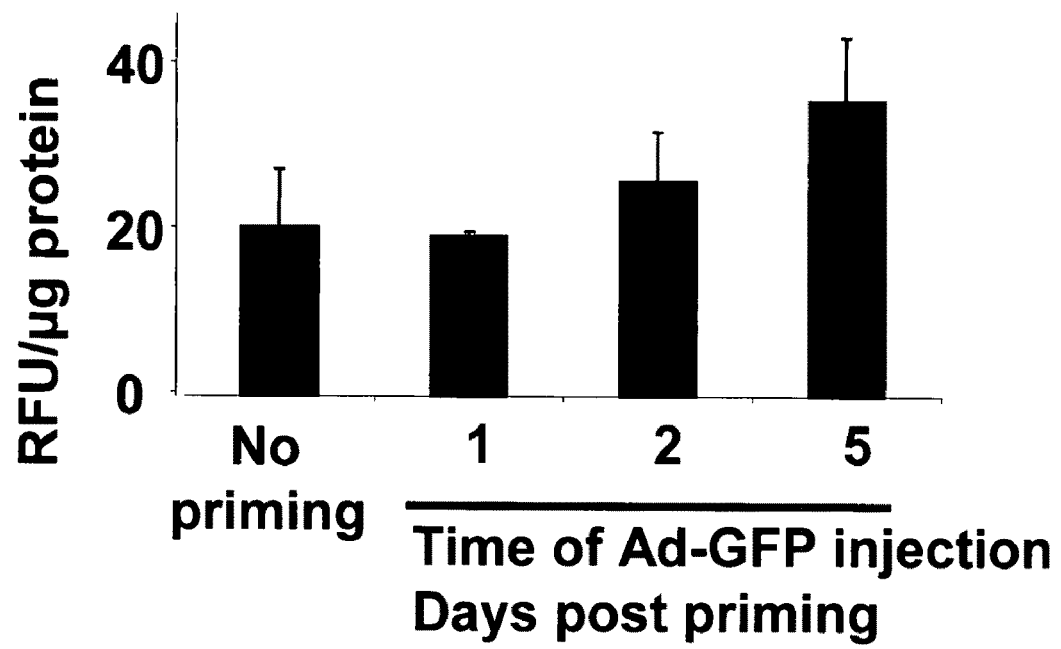
FIG. 1. Enhanced Delivery of Gene Therapy by Tumor Priming.

Effect of PLGA microparticle size. Applicants compared the distribution of two microparticle preparations with different diameters, i.e., ~3 and ~30 μm, after intraperitoneal administration. These microparticles were loaded with acridine orange and, therefore, could be visualized under UV light. After 24 hours, mice were euthanized and the abdomen was opened (three mice per formulation). FIG. 1 shows the results. The small microparticles were found in the omentum, mesentery, diaphragm and lower abdomen, whereas the large microparticles were localized in the lower abdomen.

Effect of glass transition temperature on lymphatic clearance of microparticles from peritoneal cavity. Applicants evaluated the effect of glass transition temperature (Tg) on the clearance of microparticles from the peritoneal cavity by the lymphatic flow. Mice were given intraperitoneal injections of a mixture of 75:25 LA:GA (i.e., Batch 1 in Table 1) and 50:50 LA:GA (i.e., Batch 8 in Table 1) microparticles. The 50:50 and 75:25 microparticles were of the same size (3 μm diameter), but differed in their Tg. Tg determines polymer chain motion; movements occur at temperature above Tg but not below Tg. Movement of polymer segments results in aggregation and adhesion of microparticles. Hence, the 50:50 LA:GA microparticles with a Tg lower than the body temperature (i.e., 30° C. vs 37° C.) form aggregates after being administered intraperitoneally, whereas the 75:25 LA:GA microparticles with a Tg above the body temperature (i.e., 53° C.) do not. Aggregation of microparticles results in larger effective diameter. The 75:25 LA:GA microparticles contained acridine orange (green fluorescence) whereas the 50:50 LA:GA microparticles contained rhodamine (red fluorescence).

After injections, mice were euthanized and the diaphragms were excised and rinsed with water. One-half of the diaphragms were frozen and the frozen sections were examined by fluorescence microscopy. The other half was fixed in formalin and analyzed using scanning electron microscopy. Both analyses showed a few microparticles in lymphatic vessels inside the diaphragm at 1 hour and significantly more microparticles at 24 hours, indicating that microsphere drainage into the lymphatic system increased with time. In both 1 and 24 hour samples, there were about three-fold more 75:25 LA:GA microparticles in lymphatic vessels compared to the 50:50 LA:GA microparticles. Similar findings were obtained in the mediastinal lymph nodes, confirming the lower lymphatic clearance of the 50:50 LA:GA microparticles.

TABLE 1

Properties and activity of paclitaxel-loaded PLGA microparticles
Inherent viscosity is directly related to glass transition temperature (Tg).

| Batch no. & preparation method | Inherent Viscosity (dl/g) | Tg (° C.) | LA:GA ratio | Diameter (μm) (Mean ± SD) | Actual Loading (%) | Yield (%) | Entrapment Efficiency (%) | Cumulative Release (%) 1 day | Cumulative Release (%) 49 days | $IC_{50}$ in SKOV3 cells (nM) |
|---|---|---|---|---|---|---|---|---|---|---|
| 1 (O/W) | 0.70 | 53 | 75:25 | 3.1 ± 1.4 | 1.81 | 72 | 65.2 | 5.7 | 31.2 | — |
| 2 (O/W) | 0.70 | 53 | 75:25 | 62.2 ± 33.3 | 1.83 | 74 | 67.7 | 0.25 | 3.7 | >1000 |
| 3 (W/O/W) | 0.70 | 53 | 75:25 | 35.0 ± 21.9 | 1.08 | 73 | 39.4 | 3.8 | 19.8 | — |
| 4 (O/W) | 0.70 | 53 | 75:25 | 4.2 ± 2.1 | 3.91 | 72 | 56.3 | 4.7 | 28.7 | 107.8 |
| 5 (O/W) | 0.44 | 47 | 50:50 | 36.8 ± 14.7 | 4.95 | 75 | 74.3 | 4.5 | 37.6 | — |
| 6 (O/W) | 0.18 | 30 | 50:50 | 30.4 ± 22.0 | 3.53 | 71 | 50.1 | 13.6 | 72.6 | 18.5 |
| 7 (W/O/W) | 0.18 | 30 | 50:50 | 36.0 ± 20.4 | 4.05 | 62 | 50.2 | 18.7 | 71.7 | — |
| 8 (O/W) | 0.18 | 30 | 50:50 | 3.8 ± 2.6 | 4.25 | 72 | 61.2 | 70.5 | 96.6 | 5.0 |

Preferential retention of PLGA microparticles in peritoneal cavity. Localization and disposition of PLGA microparticles within the peritoneal cavity after intraperitoneal administration was studied using rhodamine-loaded fluorescence microparticles. The disposition was compared with that of rhodamine in solution. Rhodamine-loaded microparticles (3 μm diameter, 50:50 LA:GA) were initially distributed throughout the intraperitoneal cavity (e.g., at 15 minutes), and then subsequently localized in the mesentery, omentum, and diaphragm (e.g., at 24 hours and 96 hours). In contrast, rhodamine in solution was widely distributed through the intraperitoneal cavity at 15 minutes, but the fluorescence associated with rhodamine could no longer be observed in the peritoneal cavity at 24 hours. This data indicates that the particles were preferentially retained in the peritoneal cavity compared to a solution.

Preferential localization of PLGA microparticles on peritoneal tumor nodules. Localization and disposition of PLGA microparticles within the peritoneal cavity after intraperitoneal administration was studied using acridine orange-labeled fluorescent microparticles. These particles were ~3 μm in diameter and consisted of 50:50 LA:GA. A mouse was implanted intraperitoneally with a cell suspension of human pancreatic HS 766 T-cells. A dose of acridine orange-labeled microparticles was administered intraperitoneally on day 21 or when the disease was at a late stage (median survival time is 24 days). On day 24, the animal was anesthetized, the abdominal cavity opened, and the distribution of microparticles evaluated by their fluorescence. The left panel of FIG. 1 shows the distribution of tumor nodules within the peritoneal cavity; tumors were localized primarily in the mesentery, on the omentum, and on the diaphragm. The right panel of FIG. 1 shows the localization of the green fluorescent fluorescein isothiocyanate (FITC)-labeled microparticles on tumor nodules disseminated throughout the peritoneal cavity. Analogous studies using rhodamine or acridine orange to label the same PLGA microparticles yielded similar results. In contrast, administration of these fluorescent dyes in solution (i.e., not bound to microparticles) did not show localization on tumor tissues, indicating that the localization is a unique property of the microparticles. This property is advantageous as it provides active tumor targeting.

Summary. Based on these discoveries, Applicants determined that agents loaded into PLGA microparticles are preferentially retained in the peritoneal cavity compared to agents in solution (e.g., not associated with particles), that microparticles consisting of 50:50 LA:GA are slowly drained from the peritoneal cavity by the lymphatic drainage, that small particles (~3 μm in diameter) are more evenly distributed within the peritoneal cavity compared to large particles (~30 μm diameter), that PLGA particles with a lower Tg are preferentially localized in the peritoneal cavity as compared to PLGA particles with a higher Tg, that the particle size determines the clearance by lymphatic drainage and/or absorption through the peritoneal membrane, and that PLGA microparticles (~3 μm diameter, 50:50 LA:GA) are preferentially localized on tumor nodules in the peritoneal cavity.

EXAMPLE 4

Paclitaxel-Loaded PLGA Microparticles

This example demonstrates the methods for preparing the paclitaxel-loaded PLGA microparticles and characterization of the PLGA microparticles. PLGA is a copolymer consisting of various ratios of lactic acid or lactide and glycolic acid or glycolide. This example further demonstrates the effects of microparticle properties on the drug release from the microparticles, to aid the discovery of the PLGA microparticles that provide the desired drug release rates. Paclitaxel was used as the example of the drug loaded in the microparticles. Similar procedures can be used to load other drugs or agents into these microparticles.

Preparation. Applicants used the emulsion/evaporation method to prepare the paclitaxel-loaded PLGA microparticles. Briefly, for the water-in-oil-in-water (W/O/W) double emulsion method, PLGA and paclitaxel were codissolved in 5 ml of methylene chloride. The solution was emulsified in 1 ml of water by homogenization for 30 seconds and added to 20 ml of 1% polyvinyl alcohol (PVA) solution. For the oil-in-water (O/W) emulsion method, the drug-polymer solution was directly added to 20 ml of 1% PVA solution. For both methods, the resulting emulsion was diluted into 500 ml of 0.1% PVA solution preheated at 38° C. and stirred continuously until solvent evaporation was completed. After 30 minutes, microparticles were collected by centrifugation, washed three times with water, and lyophilized.

For determination of the drug load, microparticles were dissolved in acetonitrile. The internal standard, cephalomannine (100 μl of 20 μg/ml methanol) was added. The mixture was allowed to dry under a stream of air. The residue was reconstituted in 0.1 ml of acetonitrile followed by the addition of 0.1 ml of water. After centrifugation, the supernatant was analyzed for paclitaxel concentration using high performance liquid chromatography. Reference samples, consisted of mixtures of blank PLGA microspheres and known amounts of paclitaxel, were processed similarly. The ratio of the paclitaxel concentration in the drug-loaded microparticle supernatant to the paclitaxel concentration in the reference sample indicated the drug load.

Characterization. The surface morphology and internal structure of paclitaxel-loaded PLGA microparticles were studied using scanning electron microscopy. Microparticles were spherical in shape and smooth on the surface. Microparticles prepared using the O/W method (Batch 2) showed a homogenous, filled internal structure, whereas microparticles prepared using the O/W/O method (Batch 3) showed a porous, multi-compartmental internal structure. Table 1 shows the characteristics of paclitaxel-loaded microparticles.

Identifying the PLGA microparticle properties that yield the desired drug release rate. Applicants evaluated the relationship between microparticle properties and the release of paclitaxel in phosphate-buffered saline containing 0.1% of Tween 80 (pH 7.4) at 37° C. The results outlined below indicate that the rate and extent of paclitaxel release from microparticles can be fine-tuned by altering the properties of microparticles.

Effect of PLGA particle size. The rate and extent of release were inversely related to the size of microparticles. For example, for microparticles prepared using 50:50 molar ratio of LA:GA, Batch 8 which had a diameter of ~4 μm showed higher release compared to Batch 6 which had a larger diameter of ~30 μm. Similarly, Batch 1, which differed from Batch 2 only in size (~3 versus ~60 μm in diameter), showed more rapid release. Smaller microparticles had a higher surface area-to-volume ratio compared to large microparticles. Increase in surface area results in greater exposure of paclitaxel to the aqueous media, causing a larger initial burst. Moreover, smaller microparticles have shorter diffusion path lengths, resulting in more rapid drug release and matrix degradation.

Effect of internal structure of PLGA microparticles. Microparticles with porous, multi-compartment structure showed a higher release rate compared to the microparticles with filled structure. This is likely caused by the shorter diffusion path lengths in the multi-compartmental microparticles. For example, with 50:50 LA:GA as carriers, the microparticles with a multi-compartment internal structure showed a higher initial release compared to microparticles with a filled internal structure (i.e., Batch 7 vs Batch 6). Likewise, with 75:25 LA:GA as carriers, the microparticles with a multi-compartmental internal structure showed a faster release compared to microparticles with a filled internal structure (i.e., Batch 3 vs. Batch 2).

Effect of inherent viscosity of PLGA microparticles. The inherent viscosity, which is determined by the polymer molecular weight, is inversely related to the release rate. For example, Batches 3 and 7 were prepared using W/O/W and had the same particle size. Batch 3, which showed a higher inherent viscosity, released paclitaxel 3.5-fold slower.

Effect of polymer composition of PLGA microparticles. Microparticles prepared with 50:50 LA:GA showed higher release rates than microparticles prepared using 75:25 LA:GA. This is likely because the 50:50 LA:GA microparticles were more amorphous (i.e., lower crystallinity). Because of its low aqueous solubility, fluid diffusion into or out of microparticles plays a role in the release of paclitaxel from microparticles. A decrease in crystallinity enhances the diffusion of fluid into the microparticles. Enhanced fluid diffusion also accelerates the degradation of polymers, resulting in faster drug release (Alonso, et al., *Vaccine,* 12: 299-306, 1994).

EXAMPLE 5

Tumor-Penetrating Paclitaxel-Loaded PLGA Microparticles

This example demonstrates the use of a mixture of microparticle formulations with different drug release profiles where one formulation releases paclitaxel rapidly (e.g., 70% within 24 hours) to induce apoptosis and thereby enhances the tumor penetration of PLGA microparticles.

Penetration of microparticles in peritoneal tumors. A mouse was implanted intraperitoneally with human Hs766T pancreatic xenograft tumor cells. When intraperitoneal tumors had established (day 21), the animal was treated with a dose of paclitaxel-loaded microparticles of ~3 μm diameter, which were acridine orange-labeled for easy detection of particle penetration into the tumors. These microparticles released paclitaxel rapidly (~70% in 24 hr) and, thereby, induced apoptosis, which in turn facilitated the penetration of microparticles into the tumors. Another group of animals were treated with blank microparticles prepared using the same methods but without paclitaxel. On day 24, the omentum and attached tumors were harvested. The omentum is the ligament separating the peritoneal cavity and retroperitoneum, and a site of tumor concentration in mice and human patients. The tumors were frozen and sectioned. Particle penetration at different depths into the tumor was determined by fluorescence microscopy, which visualized the acridine orange-labeled particles. FIG. 2 shows the results. Particle penetration was extensive and the distribution was evenly throughout the solid tumor. In contrast, in tumors from animals treated with blank microparticles without the tumor priming treatment with paclitaxel, the microparticles remained in the tumor periphery.

Paclitaxel concentrations in peritoneal tumors. Applicants compared the concentrations of paclitaxel in solid tumors located on the omentum, after IP instillation of paclitaxel-loaded microparticles (Batch 8) or Taxol®. The peak paclitaxel concentration derived from the microparticles was significantly higher (13 μg/g) and attained at a later time (i.e., 3 days) compared to the commercial Taxol® formulation (3.2 μg/g attained at 24 hours). These concentrations are the total of free and entrapped drug. The area-under-concentration-time-curve, which is indicative of the total drug exposure, calculated using the linear trapezoidal rule, was 16-fold higher for the microparticles (82 vs 5 μg-day/g), thus indicating the significant tumor targeting advantage of the paclitaxel-loaded PLGA microparticles.

EXAMPLE 6

Biological Activity of Paclitaxel-Loaded PLGA Microparticles

This example demonstrates that paclitaxel-loaded PLGA microparticles are biologically active, under in vitro and in vivo conditions. There is no change in biological activity for paclitaxel after encapsulation into microspheres. Also, paclitaxel loaded PLGA microspheres, due to its tumor targeting property and its sustained retention in the tumor, showed superior in vivo efficacy to the commercial Taxol® formulation.

In vitro biological activity. This was studied using human ovarian SKOV3 cancer cells. Drug effect was measured using the sulforhodamine B assay (Au, et al., *Cancer Chemother. Pharmacol.,* 41: 69-74, 1997). The study compared the concentration-response curves of free paclitaxel in an aqueous solution (i.e., paclitaxel dissolved in culture medium) and four paclitaxel-loaded PLGA microparticle formulations (i.e., Batch 2, 4, 6, and 8 in Table 1), after 96-hour treatment. The rank order of biological activity of the 4 preparations is identical to the rank order of the drug release rate, with the rapid release preparations being more active. For example, Batch 8 which released 81.5% in 96 hr was the most active, followed by Batch 6 which released 28.5% and Batch 4 which released 10.9%. Batch 2 which released 0.25% had no cytotoxic effect. The respective concentrations required for 50% cytotoxicity were 5.0, 18.5, 108, and >1000 nM.

In vivo biological activity. Applicants compared the antitumor activity of paclitaxel PLGA microparticles to that of the commercial Taxol® formulation. The doses were 120 mg/kg paclitaxel-equivalents for the microparticles and 40 mg/kg for Taxol®. At these doses, these two formulations were equi-toxic and produced about 10% body weight loss in two days, after which the animals recovered their weight. The microparticles consisted of three formulations, one that released paclitaxel rapidly (Batch 8, 70.5% in 1 day) and two that released paclitaxel slowly (Batch 6, 72.6% in 49 days, and Batch 4, 28.7% in 49 days). Particle properties are more fully described in Example 2. The results show significant survival advantage for the microparticles; the median survival time was 47 days for the vehicle-treated control group, 85.5 days for the Taxol® group, and 115.5 days for the microparticles group (p<0.01 for the difference between Taxol® and microparticles). Note that this study was conducted in late stage disease (4 weeks after implantation), and used a combination of two slow-release microparticles with different sizes (approximately 3 to 4 μm and approximately 30 μm).

Similar results were obtained in animals bearing peritoneal advanced pancreatic cancer. Mice were implanted with IP human pancreatic Hs766T tumors. After the tumors had established, on day 10 after tumor implantation, animals were treated with physiologic saline, Taxol® (60 mg/kg), or paclitaxel particles (combination of a rapid release and two slow-release preparations). The respective median survival times were 24, 33, and 57 days. Blank microparticles showed similar data as saline control.

Plasma and tissue concentrations after administration of the two formulations. The paclitaxel concentrations in plasma and intraperitoneal tissues were determined using a high performance liquid chromatography assay, and the area-under-the-concentration-time curve (AUC) from time zero to time 168 hours was calculated using the linear trapezoidal rule. The results are shown in Table 2, and indicate that administration of paclitaxel loaded into PLGA microparticles yielded a 2.5 to 6-fold higher concentration in peritoneal tissues when compared to Taxol®. At the same time, plasma concentrations were only elevated 1.5-fold, indicating a preferential tissue targeting by the use of paclitaxel microparticles.

TABLE 2

Paclitaxel concentrations in plasma and intraperitoneal tissues after intraperitoneal administration of equitoxic doses of paclitaxel formulated as microparticles (120 mg/kg) or Taxol ® (40 mg/kg). $AUC_{0 \to 168\ Hours}$ was calculated using the linear trapezoidal rule.

| Tissue | $AUC_{0 \to 168\ Hours}$ (µg/g * hr) | | |
|---|---|---|---|
|  | Microparticles | Taxol | Ratio |
| Plasma* | 8.15 | 5.43 | 1.50 |
| Peritoneal Lavage** | 960 | 257 | 3.73 |
| Liver | 319 | 130 | 2.46 |
| Small Intestine | 210 | 60.2 | 3.49 |
| Large Intestine | 171 | 38.3 | 4.48 |
| Connective Tissue | 1389 | 227 | 6.12 |

*Plasma AUC = (µg/ml * hr)
**Peritoneal Lavage AUC = (% of initial dose * hr)

This study used single and equi-toxic doses of the microparticles and Taxol®. By this criterion, the paclitaxel-equivalent dose for the microparticles was higher than the dose for Taxol®. This is because sustained release of drug reduced the dose intensity and, therefore, reduced the toxicity and increased the maximally tolerated dose. While repeated administration of Taxol® might have improved the treatment outcome in this group, repeated administration was not needed for the paclitaxel-loaded microparticles. The latter represents one of the advantages of microparticles, which is to reduce the need of frequent dosing.

EXAMPLE 7

Preparation and Characterization of Paclitaxel-Loaded Gelatin Nanoparticles

This example demonstrates the preparation and characterization of paclitaxel-loaded gelatin nanoparticles.

Preparation of paclitaxel-loaded gelatin nanoparticles. Nanoparticles were prepared using several preparations of gelatin with different bloom numbers (75-100, 175, and 300), and using the desolvation method (Oppenheim, R. C., Int. J. Pharm., 8: 217-234, 1981). Gelatin (200 mg) was dissolved in 10 ml water containing of 2% Tween 20. The solution was heated to 40° C. with constant stirring at 300 rpm. To this solution, 2 ml of a 20% aqueous solution of sodium sulfate was added slowly, followed by 1 ml isopropanol containing 2 mg of paclitaxel. A second aliquot of sodium sulfate solution (5.5-6 ml) was added until the solution turned turbid which indicated the formation of gelatin aggregates. Approximately 1 ml distilled water was then added until the solution turned clear. An aqueous solution of glutaraldehyde (25%, 0.4 ml) was added to crosslink the gelatin. Sodium metabisulfite solution (12%, 5 ml) was added 5 minutes later to stop the crosslinking process. After 1 hr, the crude product was purified on a Sephadex G-50 column. The nanoparticle-containing fraction was lyophilized in a freeze-drier over 48 hours.

Preparation of poly(lysine) coated and paclitaxel-loaded gelatin nanoparticles. Nanoparticles were prepared using similar method as the non-coated nanoparticles. During the late stage of the crosslinking after the nanoparticle is formed, poly(lysine) was added in a weight equivalent to about 5% to about 10% of the weight of the gelatin, resulting in poly(lysine)-coated nanoparticles. The purification step was identical to the step used for non-coated nanoparticles described above.

Determination of paclitaxel loading in gelatin nanoparticles. Two mg of paclitaxel-loaded nanoparticles were dispersed in 0.5 ml phosphate-buffered saline (PBS), and digested with 0.5 ml pronase (1 mg/ml in PBS) in a metabolic shaker at 37° C. After about 1 hour or when a clear solution was obtained, the internal standard, cephalomannine (50 µl of 20 µg/ml methanol) was added, followed by extraction with two volume of 3 ml ethyl acetate each. The ethyl acetate layers were pooled, dried under a stream of air, and reconstituted in acetonitrile. The paclitaxel concentrations in the extracts were compared to the concentrations in reference samples to determine the paclitaxel loading. The reference samples, consisting of mixtures of blank gelatin nanoparticles and known amounts of paclitaxel, were processed as described for the nanoparticles.

Table 3 shows the physical properties of different preparations of paclitaxel nanoparticles. The yield of nanoparticles ranged from 40 to 82%, and decreased with increasing molecular weight of gelatin. The actual drug loading was between 33 to 78% of the theoretical loading.

TABLE 3

Loading Efficiency Of Paclitaxel-Loaded Gelatin Nanoparticles
A higher bloom number indicates a higher molecular weight
(Mean ∀ standard deviation of 3 preparations)

| Gelatin molecular weight (Bloom No.) | Yield* (%) | Theoretical loading, (wt %) | Actual loading (wt %) |
|---|---|---|---|
| 75-100 | 75.9 ± 8.0 | 0.99 | 0.46 ± 0.08 |
| 175 | 82.7 ± 7.5 | 0.99 | 0.74 ± 0.07 |
| 300 | 52.0 ± 7.5 | 0.99 | 0.33 ± 0.05 |
| 175 | 56.6 ± 9.3 | 1.96 | 1.54 ± 0.09 |
| 300 | 39.7 ± 8.6 | 1.96 | 0.76 ± 0.06 |

*Yield is the weight of freeze-dried gelatin nanoparticles obtained after preparation and gel filtration, expressed as percent of the starting weight of gelatin.

Nanoparticles prepared using high molecular weight gelatin formed large aggregates; the diameter of aggregates ranged from 10 µm to >30 µm. Removal of these aggregates during the column chromatographic purification step resulted in low yield and low drug entrapment efficiency. Low entrapment efficiency was also observed in nanoparticles prepared using low molecular weight gelatin. Optimal and highest yield and entrapment efficiency were achieved using the medium molecular weight gelatin (175 bloom). Subsequent studies used gelatin with 175 bloom to prepare paclitaxel-loaded nanoparticles.

Characterization of Paclitaxel-loaded nanoparticles. A mixture of gelatin nanoparticles and distilled water (~50 µl) was placed on foil paper, dried, coated with gold, and observed under a Philips XL 30 scanning electron microscope (SEM). For particle size distribution, over 1,000 nanoparticles were examined using SEM images taken from 4-6 fields. The production yield was calculated from the weight of freeze-dried gelatin nanoparticles, and was expressed as percent of the starting weight of gelatin. The SEM results showed that the nanoparticles are spherical in shape, with a mean size ranging from 600 to 1,000 nm.

Wide-angle X-ray diffraction (WAXD) spectra of pure paclitaxel, mixtures of paclitaxel (2%, in weight %) and blank gelatin nanoparticles, and paclitaxel-loaded nanoparticles (1.62% loading), were obtained using Scintag PAD-V diffractometer. The samples were scanned from 5° to 60° with a scanning rate of 1°/min. The WAXD results showed sharp peaks in X-ray diffraction spectra for free paclitaxel and mixture of free paclitaxel and blank gelatin nanoparticles, but not for paclitaxel-loaded gelatin nanoparticles. This indicates that the paclitaxel entrapped in the nanoparticles existed in the amorphous state and not the crystalline state. The amorphous state is desired, due to its rapid dissolution rate.

Release of paclitaxel from gelatin nanoparticles. Paclitaxel nanoparticles (12 mg) was dispersed in 100 ml PBS and incubated at 37° C. Serial samples (1 ml) were withdrawn and centrifuged for 15 min at 40,000 rpm using a Beckman L-70 ultracentrifuge. Four hundred µl of the nanoparticle-free supernatant was removed and extracted with 3 ml ethyl acetate twice. The ethyl acetate extract was analyzed for paclitaxel concentration by high performance liquid chromatography.

Results of the adsorption study indicated that about 4.5% of the total amount of paclitaxel loaded in nanoparticles was adsorbed on the nanoparticles. Release of paclitaxel from nanoparticles into PBS was rapid, with 55%, 87%, and 92% released after 15 minutes, 2 hours, and 3 hours at 37° C., respectively.

Biological activity of paclitaxel-loaded nanoparticles. Human RT4 bladder transitional bladder cancer cells were obtained from the American Type Culture Collection (Rockville, Md.) and cultured in McCoy's medium supplemented with 9% fetal bovine serum, 2 mM L-glutamine, 90 µg/ml gentamicin, and 90 µg/ml cefotaxime sodium, at 37° C. in a humidified atmosphere of 5% $CO_2$ in air. Cells were harvested from subconfluent cultures using trypsin and resuspended in fresh medium. Cells with more than 90% viability, as determined by trypan blue exclusion, were used. Cells were seeded in 96-well microtiter plates (~2,000 cells/well) and allowed to attach to the plate surface for 24 hours. Applicants have shown that paclitaxel produces immediate and delayed cytotoxicity (Au, et al., *Cancer Res.*, 58: 2141-2148, 1998). For immediate effect evaluation, cells were incubated with 0.2 ml culture medium containing an aliquot of an aqueous solution of paclitaxel (referred to as free paclitaxel) or paclitaxel-loaded nanoparticles at equivalent paclitaxel doses for 48 and 96 hours. Drug effect was measured immediately after treatment. For delayed effect evaluation, cells were treated similarly for 15 minutes and 2 hours, washed with PBS once, and then incubated with drug-free medium for a total of 96 hours, at which time the drug effect was measured.

For the free drug, stock solutions of paclitaxel were prepared by first dissolving paclitaxel in ethanol followed by serial dilution using culture medium. The final ethanol concentration was less than 0.1%.

The cell number remaining after treatment was measured using the sulforhodamine B assay (Au, et al., *Cancer Chemother. Pharmacol.*, 41: 69-74, 1997). The sigmoidal concentration-response curves were analyzed to obtain the drug concentrations producing 50% inhibition ($IC_{50}$), using nonlinear regression.

For the immediate effect, treatments with either free or nanoparticle-entrapped paclitaxel resulted in maximal inhibition of 60% at 48 hours and 84% at 96 hours. The increase in maximum paclitaxel cytotoxicity with treatment time is consistent with Applicants' previous observations (Au, et al., *Cancer Res.*, 58: 2141-2148, 1998). For the 48 and 96 hour treatments, the respective $IC_{50}$ values were 11.0±0.4 and 4.0±0.4 nM for free paclitaxel, and 9.6±1.1 and 4.0±0.3 nM paclitaxel-equivalents for paclitaxel-loaded nanoparticles (mean±SD of three experiments for both preparations). The differences between the $IC_{50}$ values for these two preparations are not significant (p=0.15 for 48 hr and p=0.71 for 96 hr, unpaired t-test).

For the delayed effect (i.e., effect measured at 96 hours), treatments with either free or nanoparticle-entrapped paclitaxel for 15 minutes and 2 hours resulted in maximal inhibition of 74% to 85%. For the 15 minute and 2 hour treatments, the respective $IC_{50}$ values were 156.7±6.6 and 33.0±4.8 nM for free paclitaxel, and 165.7±33.5 and 31.4±1.8 nM paclitaxel-equivalents for paclitaxel-loaded nanoparticles (mean±SD of three experiments for both preparations). The differences between the corresponding $IC_{50}$ values for the two preparations also are not significant (p=0.70 for 15 minute treatment and p=0.64 for 2 hour treatment, unpaired t-test). This data indicate rapid release of paclitaxel from the nanoparticles and that the paclitaxel-loaded nanoparticles are equally effective as free paclitaxel dissolved in ethanol and water (in the absence of Cremophor).

EXAMPLE 8

Delivery of High Paclitaxel Concentrations to the Bladder Wall after Intravesical Instillation of Paclitaxel-Loaded Gelatin Nanoparticles This example demonstrates that the paclitaxel-loaded gelatin nanoparticles, when instilled into a bladder cavity, deliver high concentrations of paclitaxel to bladder tissues.

The determination of the delivery of paclitaxel to bladder tissues, after instillation of paclitaxel-loaded gelatin nanoparticles, was performed as described elsewhere (Wientjes, et al., *Cancer Res.*, 51: 43474354, 1991; Song, D., et al., *Cancer Chemother. Pharmacol.*, 40: 285-292, 1997). Briefly, a solution of paclitaxel-loaded gelatin nanoparticles (containing 1 mg paclitaxel in a total weight of 250 mg) was instilled into the bladder of an anesthetized dog, for a period of two hours. Afterward, the bladder was removed, flash frozen, and sectioned in parallel to the urothelial surface into 40-µm slices using a cryotome. After weighing, the frozen tissue samples were analyzed for paclitaxel concentration using a high performance liquid chromatographic assay, as described previously (Song and Au, *J. Chromatogr.*, 663: 337-344, 1995). The results show that the paclitaxel concentrations in the bladder wall declined from about 50 µg/g (approximately equal to 60 µM) in the urothelium, i.e., the inner surface of the bladder, to about 1 µg/g at a depth of 500 µm away from the urothelium, and remained relatively constant at approximately 0.5 µg/g for tissue depths greater than 500 µm. The urothelial concentration exceeded the unbound concentration in urine by approximately 20-fold, indicating good penetration of paclitaxel into the bladder wall. These tissue concentrations also exceeded the paclitaxel concentrations that produced cytotoxicity in human bladder RT4 cancer cells (i.e., ~33 nM for 2 hour treatment, see Example 1).

Tissue retention of paclitaxel after administration in gelatin nanoparticles was studied in other dogs by analyzing the bladder tissue concentration at 22 hours after the 2-hour treatment had ended and after the dosing solution was drained (i.e., 24 hours from the time of dose administration). The paclitaxel concentration was 0.14 µg/g (about 165 nM) in the urothelium and declined slowly to 0.01 µg/g at a depth of 500 µm. This data indicate substantial retention of paclitaxel in the bladder tissues; the half-life of drug disappearance was estimated to be ~150 minutes which is more than 30-times longer compared to the half-life of less than 5 minutes for mitomycin C in human bladder tissues (Wientjes, et al., *Cancer Res.*, 53:3314-3320, 1993).

EXAMPLE 9

Efficacy of Paclitaxel-Loaded Gelatin Nanoparticles in Histocultures Derived from Bladder Tumors of Dog Patients Bladder tumors were obtained by transurethral resection from the bladders of three dog patients diagnosed with bladder cancer. The tumors were sectioned in 1 mm pieces, cultured on collagen gel as histocultures (Au, et al., *Cancer Chemother. Pharmacol.*, 41: 69-74, 1997), and treated with paclitaxel-loaded nanoparticles for 2 hours. The $IC_{50}$ values for inhibition of bromodeoxyuridine labeling, expressed as paclitaxel-equivalents, were 2.2 µM in the tumor from one dog tumor and >10 µM in the tumors from the remaining two dogs.

A three-way comparison of the $IC_{50}$ values, the drug concentrations in the bladder tissues (see Example 8), and the clinical outcome in these three dogs (see Example 10) shows that the dog with the most sensitive tumor (i.e., the lowest $IC_{50}$ value), and, therefore, would have received sufficient drug to produce therapeutic benefits, responded favorably to treatment with paclitaxel-loaded nanoparticles where the tumor size was reduced by greater than 50%. In contrast, the $IC_{50}$ values in the remaining two dogs exceeded the attainable bladder tissue concentrations and the tumors in these animals showed progressive disease (i.e., increase in size by more than 50% (Helfand, et al., *J. Am. Anim. Hosp. Assoc.*, 30: 270-275, 1994).

This example shows sensitivity of bladder tumors to paclitaxel formulated in gelatin nanoparticles, and correlation between in vitro and in vivo results. It is noteworthy that the $IC_{50}$ values of paclitaxel in human superficial bladder tumors are lower than in dogs, and that bladder tumors in human patients that are candidate for direct intravesical instillation are superficial, not penetrating beyond the mucosal layer of the bladder wall. The $IC_{50}$ values obtained previously by Applicants for human bladder tumors are 1.2 µM for stage of T0 and T1 bladder tumors obtained from human patients (calculated from data in Au, et al., *Cancer Chemother Pharmacol.*, 41:69-74, 1997). This suggests that clinical results in human patients will be better than in dogs.

EXAMPLE 10

Efficacy of Paclitaxel-Loaded Gelatin Nanoparticles in Dog Patients with Bladder Cancer Dogs with transitional cell carcinoma (TCC) of the bladder and no evidence of metastases were eligible. One milligram of paclitaxel-loaded gelatin nanoparticles in a 20-ml saline suspension was administered intravesically through a Foley catheter under general anesthesia, once weekly for 3 weeks. The dose was 1 mg paclitaxel in 250 mg gelatin. All patients received prophylactic antibiotics and deracoxib. Blood and urine samples were collected before and during the 2-hour treatment period. Urine and tissue paclitaxel concentrations were analyzed by column-switching HPLC. Abdominal ultrasonography was used to monitor tumor response.

Six dogs were treated; four patients had no prior therapy. Plasma concentrations were below the HPLC detection limit at all time points. Mean initial and final urine concentrations were 27.51±8.59 g/ml (n=16) and 11.16±8.63 g/ml (n=15), respectively. Concentrations of unbound paclitaxel remained constant at a concentration of 0.8-1 µg/ml, which is approximately the maximal water solubility of paclitaxel at body temperature. The overall response was 2 partial responses, 2 patients with stable disease (i.e., not partial response and not progressive disease), and 2 patients with progressive disease; the definition of clinical response or outcome is as described in Example 9. There was no evidence of systemic drug absorption or toxicity. The objective response rate of 2/6 (33%) of the patients, which is higher than the response rate (12.5%) reported in the literature for intravesical treatments using other chemotherapeutic agents (range of 0-20%, average of 12.5%; Mutsaers, et al., *J. Vet. Intern. Med.*, 17:136-144, 2003).

EXAMPLE 11

Kidney Targeting by Gelatin Nanoparticles after Intravenous Administration

The kidney targeting advantage by the gelatin nanoparticles was studied by comparing the distribution of paclitaxel-loaded gelatin nanoparticles to the distribution of the commercial TAXOL® brand paclitaxel formulation. The gelatin nanoparticles were prepared and administered to mice intravenously via the tail vein over 1 minute. The paclitaxel dose was 10 mg/kg. Animals were euthanized 24 hours later. The organs were removed, homogenized, extracted and analyzed for paclitaxel concentration using high performance liquid chromatography. These procedures were conducted as described in Example 7. The nanoparticles (664 nm diameter, 0.4% loading) released paclitaxel rapidly (90% in 3 hours at 37° C.). The total concentrations of paclitaxel (free and bound) in blood declined with a major half-life of 14 hr. Paclitaxel was distributed and retained in organs with the highest levels in liver, small intestine and kidney (Table 4). The ratios of tissue-to-blood concentrations were in the rank order of liver >small intestine >kidney >≧large intestine >spleen =stomach =lung >heart. This is different from the distribution of TAXOL®, which had a tissue distribution in the rank order of liver >small intestine >large intestine >stomach >lung ≧kidney ≧~spleen >heart. Selective retention was calculated as the ratio of tissue concentrations after administration in nanoparticles or after administration in TAXOL® after normalization for plasma concentrations (Table 4). Selective retention in the kidney was 9.38-fold, and was highest of all organs. The terminal half-life of the paclitaxel concentrations in the kidney after administration in nanoparticles was 13.7 hour, as compared to 1.94 hour for administration as TAXOL®. This data indicates that gelatin nanoparticles are preferentially retained in the kidney.

TABLE 4

Blood and tissue pharmacokinetics of paclitaxel delivered by the gelatin nanoparticle formulation and the Cremophor/ethanol (i.e., Taxol ®) formulations. Mice were given an intravenous dose (10 mg/kg paclitaxel-equivalents) of paclitaxel-loaded nanoparticles or paclitaxel dissolved in Cremophor and ethanol. Nine time points spanning from 5 minutes to 24 hours post-administration were studied. Three animals were used per time points. Area under the concentration-time curve (AUC) was calculated from time zero to 24 hours. For tissues that showed levels below the detection linmits (14 ng/ml for blood and 40 ng/g for tissues), we used the detection limit as the upper limit of concentration at 24 hr to calculate the $AUC_{0-24}$. In all cases, the $AUC_{0-6}$ accounted for >82% of $AUC_{0-24}$. Hence, potential erros to the approximation of $AUC_{6-24}$ are consicered minimal. The $C_{tissue}:C_{blood}$ ratio was the average value of all 9 time points.

|  | Blood | Lung | Heart | Stomach | Large intestine | liver | Spleen | Small intestine | Kidney |
|---|---|---|---|---|---|---|---|---|---|
| Nanoparticles |  |  |  |  |  |  |  |  |  |
| $AUC_{0-24}$ (:g-hr per ml or g) | 4.79 | 36.1 | 18.6 | 65.8 | 75.0 | 379 | 64.8 | 288 | 165 |
| $C_{tissue}:C_{blood}$ ratio | 1.00 | 6.87 | 2.89 | 11.9 | 21.3 | 67.0 | 12.5 | 59.3 | 30.3 |
| $AUC_{tissue}:AUC_{blood}$ ratio | 1.00 | 7.53 | 3.88 | 13.7 | 15.7 | 79.1 | 13.5 | 60.1 | 34.4 |

TABLE 4-continued

Blood and tissue pharmacokinetics of paclitaxel delivered by the gelatin nanoparticle formulation and the Cremophor/ethanol (i.e., Taxol ®) formulations. Mice were given an intravenous dose (10 mg/kg paclitaxel-equivalents) of paclitaxel-loaded nanoparticles or paclitaxel dissolved in Cremophor and ethanol. Nine time points spanning from 5 minutes to 24 hours post-administration were studied. Three animals were used per time points. Area under the concentration-time curve (AUC) was calculated from time zero to 24 hours. For tissues that showed levels below the detection linmits (14 ng/ml for blood and 40 ng/g for tissues), we used the detection limit as the upper limit of concentration at 24 hr to calculate the $AUC_{0-24}$. In all cases, the $AUC_{0-6}$ accounted for >82% of $AUC_{0-24}$. Hence, potential erros to the approximation of $AUC_{6-24}$ are consicered minimal. The $C_{tissue}:C_{blood}$ ratio was the average value of all 9 time points.

|  | Blood | Lung | Heart | Stomach | Large intestine | liver | Spleen | Small intestine | Kidney |
|---|---|---|---|---|---|---|---|---|---|
| C/E formulation |  |  |  |  |  |  |  |  |  |
| $AUC_{0-24}$ (:g-hr per ml or g) | <6.73 | <33.8 | 16.0 | 55.0 | 88.6 | 164 | <31.9 | 120 | <33.7 |
| $C_{tissue}:C_{blood}$ ratio | 1.00 | 4.20 | 1.76 | 6.78 | 9.80 | 21.9 | 2.93 | 10.5 | 3.23 |
| $AUC_{tissue}:AUC_{blood}$ ratio | 1.00 | 5.02 | 2.74 | 8.17 | 13.2 | 24.4 | 4.74 | 17.8 | 5.00 |
| Nanoparticle-to-C/E ratios |  |  |  |  |  |  |  |  |  |
| $AUC_{0-24}$ (:g-hr per ml or g) | >0.71 | >1.1 | >1.2 | 1.2 | 0.84 | 2.3 | >2.0 | 2.4 | >4.9 |
| $C_{tissue}:C_{blood}$ ratio | 1.00 | 1.64 | 1.64 | 1.76 | 2.17 | 3.06 | 4.27 | 5.65 | 9.38 |
| $AUC_{tissue}:AUC_{blood}$ ratio | 1.00 | 1.50 | 1.63 | 1.68 | 1.19 | 3.25 | 2.85 | 3.37 | 6.88 |

Equivalents

While the invention has been described with reference to various embodiments, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims. In this application all units are in the metric system and all amounts and percentages are by weight, unless otherwise expressly indicated. Also, all citations referred herein are expressly incorporated herein by reference.

We claim:

1. A composition of microparticles or nanoparticles containing an antitumor agent comprising:
   (a) microparticles ranging in particle size from about 3 to about 30 μm, that provide a fast-release formulation of a tumor apoptosis inducing agent, being formed from poly (lactide-co-glycolide) (PLGA) copolymer with a LA:GA ratio of 50:50, where the average chain lengths are such that the copolymer has a glass transition temperature (Tg) of less than about 37° C.;
   (b) nanoparticles or microparticles that provide a slow-release formulation of an antitumor agent; and
   (c) a pharmaceutically acceptable carrier.

2. The composition of claim 1, wherein said apoptosis inducing agent comprises paclitaxel.

3. The composition of claim 1, wherein said fast-release formulation releases at least 50 nM of paclitaxel over about 1 hour.

4. The composition of claim 1, wherein said apoptosis inducing agent is provided in an amount sufficient to reduce the density of the epithelial cells of a tumor by at least 20%.

5. The composition of claim 1, wherein said apoptosis inducing agent is provided in an amount sufficient to reduce the density of the epithelial cells of a tumor by at least 20%, during about 24 hours after administration.

6. The composition of claim 1, wherein said apoptosis inducing agent is provided in an amount sufficient to induce apoptosis in at least 10% of the epithelial cells of a tumor.

7. The composition of claim 1, wherein said apoptosis inducing agent is provided in an amount sufficient to induce apoptosis in at least 10% of the epithelial cells of a tumor, during about 24 hours after administration.

8. The composition of claim 1, wherein said antitumor agent is one or more of paclitaxel or doxorubicin.

9. The composition of claim 1, wherein said antitumor agent is one or more of a chemotherapeutic agent, an antibiotic, an antibody, or a gene therapy construct.

10. The composition of claim 1, which is suitable for one or more of intravenous injection, local administration, or regional administration.

11. The composition of claim 1, wherein said one or more of nanoparticles or microparticles are coated with a bioadhesive.

12. The composition of claim 1, wherein said slow-release formulation of PLGA microparticles comprise about 75:25 LA:GA.

13. The composition of claim 1, wherein said 50:50 LA:GA microparticles have about 4% paclitaxel loading.

14. The composition of claim 1, wherein the 50:50 LA:GA PLGA microparticles have a drug release rate of between about 50% to about 70% in about one day.

15. The composition of claim 1, which additionally comprises a release enhancer being one or more of Tween 20, Tween 80, isopropyl myristate, β-lactose, or diethylphthalate.

16. The composition of claim 1, wherein said tumor apoptosis inducing agent is paclitaxel or doxorubicin, and said antitumor agent is one or more of paclitaxel, carboplatin, doxorubicin, or docetaxel.

17. A composition of microparticles or nanoparticles containing an antitumor agent comprising:
   (a) gelatin nanoparticles having an average diameter ranging about 600 nm and about 1000 nm, said gelatin having a bloom number of 175, that provide a fast-release formulation of a tumor apoptosis inducing agent being paclitaxel, comprising said paclitaxel at a loading ranging between 0.4 and 2%;
   (b) nanoparticles or microparticles that provide a slow-release formulation of an antitumor agent; and
   (c) a pharmaceutically acceptable carrier.

18. The composition of claim 17, wherein said gelatin nanoparticles are coated with a bioadhesive coating.

19. The composition of claim 18, wherein said bioadhesive coating is one or more of poly(lysine), fibrinogen, a partially esterified polyacrylic acid polymer, a polysaccharide, pectin, or a mixture of sulfated sucrose and aluminum hydroxide.

20. The composition of claim 17, which is injectable directly into the bladder.

21. The composition of claim 17, wherein said paclitaxel is combined with a cosolvent.

22. The composition of claim 21, wherein said cosolvent is one or more of dimethyl sulfoxide or polyethylene glycol.

23. The composition of claim 17, wherein said composition, when instilled into the bladder cavity, releases paclitaxel at a rate that is controlled by the volume of urine present in the bladder such that the release results in a maintained solubility concentration of paclitaxel in the urine during the duration of the treatment.

24. The composition of claim 17, wherein said gelatin nanoparticles comprise said paclitaxel at a loading ranging between 0.4 and 2%.

25. The composition of claim 24, wherein said gelatin nanoparticles comprise said paclitaxel at a loading ranging between 0.5 and 1%.

26. The composition of claim 17, wherein said gelatin nanoparticles have an average diameter ranging between about 600 nm and about 1000 nm.

27. The composition of claim 17, wherein said gelatin is cross-linked and where cross-linking is achieved with glutaraldehyde.

28. A composition for delivering an antitumor agent to a patient comprising:
   (a) poly(lactide-co-glycolide) (PLGA) microparticles providing a fast release of a tumor apoptosis inducing agent, wherein said microparticles have a particle size ranging from about 3 to about 30 μm, and said poly(lactide-co-glycolide) (PLGA) has an average chain length such that the glass transition temperature (Tg) is less than about 37° C.
   (b) microparticles or nanoparticles providing a slow release of an antitumor agent; and
   (c) a pharmaceutically acceptable carrier.

29. The composition of claim 28, wherein said poly(lactide-co-glycolide) (PLGA) microparticles providing a fast release have a particle size ranging from about 3 to about 5 μm.

30. The composition of claim 28, wherein said poly(lactide-co-glycolide) (PLGA) copolymer comprises lactide and glycolide in a molar ratio of about 50:50.

31. The composition of claim 28, wherein said poly(lactide-co-glycolide) (PLGA) has a glass transition temperature (Tg) of about 30° C.

32. The composition of claim 28, wherein said tumor apoptosis inducing agent is paclitaxel.

33. The composition of claim 32, wherein the loading of paclitaxel is about 4%.

34. The composition of claim 28, wherein said fast release corresponds to a release rate of between about 20% to about 70% in one day.

35. A composition for delivering an antitumor agent to a patient having a tumor, which comprises:
   PLGA microparticles comprising about 50:50 LA:GA, where the average chain lengths are such that the copolymer has a glass transition temperature (Tg) that is below the body temperature, having an average diameter of between about 3 to 5 μm, containing about 4% paclitaxel, and having a drug release rate of about 70% in about one day.

36. The composition of claim 35, wherein said microparticles have the combined properties of:
   (1) providing a fast drug release followed by a slow drug release;
   (2) adhering selectively to tumor tissue; and
   (3) concentrating in the peritoneal cavity.

* * * * *